United States Patent
Georgiou et al.

(10) Patent No.: US 10,865,403 B2
(45) Date of Patent: Dec. 15, 2020

(54) ENGINEERED PRIMATE CYSTINE/CYSTEINE DEGRADING ENZYMES FOR THERAPEUTIC USES

(71) Applicant: Board of Regents, The University of Texas System, Austin, TX (US)

(72) Inventors: George Georgiou, Austin, TX (US); Everett Stone, Austin, TX (US); Shira Cramer, Austin, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 196 days.

(21) Appl. No.: 15/977,246

(22) Filed: May 11, 2018

(65) Prior Publication Data
US 2018/0327734 A1 Nov. 15, 2018

Related U.S. Application Data

(60) Provisional application No. 62/055,527, filed on May 12, 2017.

(51) Int. Cl.
*C12N 9/88* (2006.01)
*C07K 14/76* (2006.01)
(Continued)

(52) U.S. Cl.
CPC .............. *C12N 9/88* (2013.01); *A61B 17/225* (2013.01); *A61K 9/0019* (2013.01); *A61K 31/7076* (2013.01); *A61K 38/16* (2013.01); *A61K 38/38* (2013.01); *A61K 38/51* (2013.01); *A61K 45/06* (2013.01); *A61K 47/60* (2017.08); *A61K 47/61* (2017.08); *A61P 35/00* (2018.01);

*C07K 14/001* (2013.01); *C07K 14/76* (2013.01); *C12Y 404/01001* (2013.01); *A61K 38/00* (2013.01);
(Continued)

(58) Field of Classification Search
None
See application file for complete search history.

(56) References Cited

U.S. PATENT DOCUMENTS 4,870,287 A 9/1989 Cole et al.
5,739,169 A 4/1998 Ocain et al.
(Continued)

FOREIGN PATENT DOCUMENTS

JP 2007-500696 1/2007
JP 2013-518594 5/2013
(Continued)

OTHER PUBLICATIONS

Vasudevan et al., Textbook of Biochemistry for Medical Students, Chapter 4, pp. 40-41 (2017).*
(Continued)

*Primary Examiner* — Erin M. Bowers
(74) *Attorney, Agent, or Firm* — Parker Highlander PLLC

(57) ABSTRACT

Methods and compositions related to the engineering of a protein with L-cyst(e)ine degrading enzyme activity are described. For example, disclosed are modified cystathionine-γ-lyases comprising one or more amino acid substitutions and capable of degrading L-cyst(e)ine. Furthermore, compositions and methods are provided for the treatment of cancer and cystinuria using the disclosed modified enzymes or nucleic acids encoding said enzymes.

36 Claims, 1 Drawing Sheet
Specification includes a Sequence Listing.

(51) Int. Cl.

| | | |
|---|---|---|
| C07K 14/00 | (2006.01) | |
| A61K 47/61 | (2017.01) | |
| A61K 47/60 | (2017.01) | |
| A61P 35/00 | (2006.01) | |
| A61K 38/38 | (2006.01) | |
| A61K 38/51 | (2006.01) | |
| A61K 38/16 | (2006.01) | |
| A61K 9/00 | (2006.01) | |
| A61K 45/06 | (2006.01) | |
| A61K 31/7076 | (2006.01) | |
| A61B 17/225 | (2006.01) | |
| A61K 38/00 | (2006.01) | |

(52) U.S. Cl.
CPC ...... C07K 2319/00 (2013.01); C07K 2319/30 (2013.01)

(56) References Cited

U.S. PATENT DOCUMENTS

| | | | |
|---|---|---|---|
| 5,760,395 | A | 6/1998 | Johnstone |
| 5,824,311 | A | 10/1998 | Greene |
| 5,830,880 | A | 11/1998 | Sedlacek et al. |
| 5,846,945 | A | 12/1998 | McCormick |
| 5,889,155 | A | 3/1999 | Ashkenazi et al. |
| 8,709,407 | B2 | 4/2014 | Georgiou et al. |
| 9,279,119 | B2 | 3/2016 | Georgiou et al. |
| 9,481,877 | B2 | 11/2016 | Georgiou et al. |
| 9,624,484 | B2 | 4/2017 | Georgiou et al. |
| 9,909,163 | B2 | 3/2018 | Georgiou et al. |
| 2005/0036981 | A1 | 2/2005 | Yagi et al. |
| 2005/0036984 | A1 | 2/2005 | Harrison et al. |
| 2006/0107342 | A1 | 5/2006 | Amir |
| 2006/0275279 | A1 | 12/2006 | Rozzell |
| 2009/0304666 | A1 | 12/2009 | Harrison et al. |
| 2011/0200576 | A1* | 8/2011 | Georgiou ............... C12Q 1/10 424/94.5 |
| 2012/0156672 | A1 | 6/2012 | Otte et al. |
| 2014/0287484 | A1 | 9/2014 | Georgiou |
| 2015/0064159 | A1 | 3/2015 | Georgiou et al. |
| 2015/0064160 | A1 | 3/2015 | Georgiou |
| 2018/0002685 | A1 | 1/2018 | Georgiou et al. |
| 2018/0008681 | A1 | 1/2018 | Stone |
| 2018/0171380 | A1 | 6/2018 | Georgiou |

FOREIGN PATENT DOCUMENTS

| | | |
|---|---|---|
| WO | WO 2018/009663 | 1/1918 |
| WO | WO 2002/020807 | 3/2002 |
| WO | WO 2011/097381 | 8/2011 |
| WO | WO 2015/031726 | 3/2015 |
| WO | WO 2015/031735 | 3/2015 |

OTHER PUBLICATIONS

"Cystathionine gamma-lyase [Rattus norvegicus]" Genbank ID No. BAB19922.2, Apr. 20, 2001.
"Cystathionine gamma-lyase homolog [imported]—Stenotrophomonas maltophilia" Genbank ID No. T45483, Jan. 31, 2000.
"Google Search—wei-cheng lu evolved enzymes for cancer therapeutics and orthogonal system," dated Jan. 18, 2017.
"Human recombinant Fc fused protein," Funakoshi News, Mar. 1, 2013. (Machine translation of Japanese text).
"Hypothetical protein [Pongo abelii]" Genbank ID No. CAH89476.1, May 1, 2008.
"Macaca fascicularis" Genbank ID No. AAW71993, Jan. 7, 2005.
"Pan troglodytes" Genbank ID No. XP_513486, May 13, 2011.
"Pongo abelii cystathionase (cystathionine gamma-lyase) (CTH), mRNA," Database DDBJ/EMBL/GeneBank [online], Accession No. NM_001131163, available at: http://www.ncbi.nlm.nih.gov/nuccore/197098155?sat=13&satkey=11125499, dated Aug. 20, 2008.
"Pongo abelii" Genbank ID No. NP_001124635, Mar. 10, 2011.
"Probable cystathionine gamma-lyase PA0400 [imported]—Pseudomonas aeruginosa" Genbank ID No. F83595, Sep. 15, 2000.
Antikainen et al., "Altering protein specificity: techniques and applications," *Bioorganic & Medicinal Chemistry*, 13:2701-2716, 2005.
Ashe et al., "N5-methyltetrahydrofolate: homocysteine methyltransferase activity in extracts from normal, malignant and embryonic tissue culture cells," *Biochem. Biophys. Res. Commun.*, 57:417-425, 1974.
Breillout et al., In: Methionine dependency of malignant tumors: a possible approach for therapy, Oxford University Press, 1628-1632, 1990.
Breitinger et al., "The three-dimensional structure of cystathionine β-lyase from *Arabidopsis* and its substrate specificity," *Plant Physiology*, 126:631-642, 2001.
Cramer et al., "Systemic depletion of L-cyst(e)ine with cyst(e)inase increases reactive oxygen species and suppresses tumor growth," *Nat. Med.*, 21:120-127, 2016.
Doxsee et al., "Sulfasalazine-induced cystine starvation: Potential use for prostate cancer therapy," *The Prostate*, 67:162-171, 2007.
Ercolani et al., "Bladder outlet obstruction in male cystinuria mice," *Int. Urol. Nephrol.*, 42:57-63, 2010.
Esaki and Soda, "L-methionine gamma-lyase from *Pseudomonas putida* and *Aeromonas*," *Methods Enzymol.*, 143:459-465, 1987.
Extended European Search Report issued in European Application No. 14 84 1106, dated Jan. 30, 2017.
Feliubadalo et al., "Slc7a9-deficient mice develop cystinuria non-I and cystine urolithiasis," *Hum. Mol. Genet.*, 12:2097-2108, 2003.
Glode et al., "Cysteine auxotrophy of human leukemic lymphoblasts is associated with decreased amounts of intracellular cystathionase protein," *Biochemistry*, 20(5):1306-1311, 1981.
Goyer et al. "Functional Characterization of a Methionine gamma-Lyase in *Arabidopsis* and its Implication in an Alternative to the Reverse Trans-sulfuration Pathway," *Plant Cell Physiol.*, 48(2):232-242 (2007).
Guan et al., "The x c—cystine/glutamate antiporter as a potential therapeutic target for small-cell lung cancer: use of sulfasalazine," *Cancer Chemotherapy & Pharmacology*, 64(3):463-472, 2009.
Halpern et al., "The effect of replacement of methionine by homocystine on survival of malignant and normal adult mammalian cells in culture," *Proc. Natl. Acad. Sci. USA*, 71:1133-1136, 1974.
Hori et al., "Gene cloning and characterization of Pseudomonas putida L-methionine-alpha-deamino-gamma-mercaptomethane-lyase," *Cancer Res.*, 56:2116-2122, 1996.
Huang et al., "Site-directed mutagenesis on human cystathionine-gamma-lyase reveals insights into the modulation of H2S production," *Journal of Molecular Biology*, 396(3):708-718, 2009.
International Search Report and Written Opinion issued in International Application No. PCT/US2017/040897, dated Oct. 10, 2017.
International Search Report and Written Opinion issued in International Application No. PCT/US2014/053359, dated Mar. 23, 2015.
International Search Report and Written Opinion issued in International Application No. PCT/US2014/053374, dated Jan. 14, 2015.
International Search Report and Written Opinion issued in International Application No. PCT/US2018/032286, dated Jul. 6, 2018.
International Search Report and Written Opinion issued in International Application No. PCT/US2018/032246, dated Aug. 1, 2018.
Invitation to Pay Additional Fees issued in International Application No. PCT/US2014/053359, dated Jan. 16, 2015.
Ito et al., "Purification and characterization of methioninase from *Pseudomonas putida*," *J. Biochem.*, 79:1263-1272, 1976.
Khersonsky et al., "Enzyme promiscuity: evolutionary and mechanistic aspects," *Current Opinion in Chemical Biology*, 10:498-508, 2006.
Kim et al., "Expression of cystathionine β-synthase is downregulated in hepatocellular carcinoma and associated with poor prognosis," *Oncology Reports*, 21(6):1449-1454, 2009.
Knoll, Thomas, et al. "Cystinuria in childhood and adolescence: recommendations for diagnosis, treatment, and follow-up," *Pediatric Nephrology* 20.1 (2005): 19-24.
Kraus et al., "Cystathionine γ-lyase: clinical, metabolic, genetic, and structural studies," *Mol. Genet. Metab.*, 97:250-259, 2009.

(56) References Cited

OTHER PUBLICATIONS

Kreis and Goodenow, "Methionine requirement and replacement by homocysteine in tissue cultures of selected rodent and human malignant and normal cells," *Cancer Res.*, 38:2259-2262, 1978.

Kreis et al., "Effect of nutritional and enzymatic methionine deprivation upon human normal and malignant cells in tissue culture," *Cancer Res.*, 40:634-641, 1980.

Kreis, "Tumor therapy by deprivation of L-methionine: rationale and results," *Cancer Treatment Rpts.*, 63:1069-1072, 1979.

Kudou et al., "Structure of the antitumour enzyme L-methionine gamma-lyase from Pseudomonas putida at 1.8 A resolution," *J. Biochem.*, 141:535-544, 2007.

Link et al., "Cystathionase: a potential cytoplasmic marker of hematopoietic differentiation," *Blut*, 47(1):31-39, 1983.

Lishko et al., "Depletion of serum methionine by methioninase in mice," *Anticancer Res.*, 13:1465-1468, 1993.

Liu et al., "Methionine dependency and the therapy of tumor," *Parenteral and Enteral Nutrition*, 12(4):247-250, 2005. (English Abstract).

Livrozet et al., "An animal model of Type A Cystinuria due to spontaneous mutation in 129S2/SvPasCrl Mice," *PLoS ONE*, 9:e102700, 2014.

Lu, "Evolved enzymes for cancer therapeutics and orthogonal system," *Dissertation—The University of Texas at Austin*, Aug. 2013.

Lu et al., "Cloning and nucleotide sequence of human liver cDNA encoding for cystathionine gamma-lyase," *Biochem. Biophys. Res. Commun.*, 189:749-758, 1992 (Abstract only).

Messerschmidt et al., "Determinants of enzymatic specificity in the Cys-Met-metabolism PLP-dependent enzymes family: crystal structure of cystathionine gamma-lyase from yeast and intrafamiliar structure comparison," *Biol. Chem.*, 384:373-386, 2003.

Motoshima et al., "Crustal structure of the pyridoxal 5'-phospate dependent L-methionine gamma-lyase from Pseudomaonas putida," *J. Biochem.*, 128(3):349-354, 2000.

Mudd et al., "Homocystinuria: an enzymatic defect," *Science*, 143:1443-1445, 1964.

Nakayama et al., "Purification of bacterial L-methionine gamma-lyase," *Anal. Biochem.*, 138:421-424, 1984.

Nygård et al., "Major lifestyle determinants of plasma total homocysteine distribution: the Hordaland Homocysteine Study," *The American Journal of Clinical Nutrition*, 67:263-270, 1998.

Office Communication issued in Australian Patent Application No. 2011212885, dated Oct. 27, 2014.

Office Communication issued in Australian Patent Application No. 2014312159, dated Aug. 10, 2018.

Office Communication issued in Canadian Patent Application No. 2,788,689, dated Dec. 27, 2017.

Office Communication issued in Chinese Patent Application No. 201180013307, dated Apr. 9, 2014.

Office Communication issued in Chinese Patent Application No. 201180013307, dated Mar. 29, 2013.

Office Communication issued in Chinese Patent Application No. 201180013307, dated Oct. 25, 2013.

Office Communication issued in European Patent Application No. 14839001.6, dated Feb. 17, 2017.

Office Communication issued in European Patent Application No. 14839001.6, dated Mar. 5, 2018.

Office Communication issued in Israeli Patent Application No. 244263, dated Sep. 16, 2018.

Office Communication issued in Japanese Patent Application No. 2012-552084, dated Aug. 24, 2015. (English translation of Japanese text).

Office Communication issued in Japanese Patent Application No. 2012-552084, dated Mar. 12, 2015. (English translation of Japanese text).

Office Communication issued in Japanese Patent Application No. 2016-537882, dated Aug. 9, 2018.

Office Communication issued in Japanese Patent Application No. 2016-537886, dated Jun. 20, 2018.

Office Communication issued in U.S. Appl. No. 13/020,268, dated Dec. 11, 2012.

Office Communication issued in U.S. Appl. No. 13/020,268, dated Jun. 18, 2013.

Office Communication issued in U.S. Appl. No. 14/472,779, dated Jun. 2, 2015.

Office Communication issued in U.S. Appl. No. 14/472,779, dated Oct. 28, 2015.

Office Communication issued in U.S. Appl. No. 14/472,750, dated Dec. 31, 2015.

Office Communication issued in U.S. Appl. No. 15/052,978, dated Jul. 6, 2017.

Office Communication issued in U.S. Appl. No. 15/451,349, dated Jul. 16, 2018.

PCT International Search Report and Written Opinion, issued in International Application No. PCT/US2011/023606, dated Oct. 25, 2011.

Paley, Olga M. Engineering a novel human methionine degrading enzyme as a broadly effective cancer therapeutic. *Dissertation—The University of Texas at Austin*, Aug. 2014.

Peters et al., "A mouse model for cystinuria type I," *Hum. Mol. Genet.*, 12:2109-2120, 2003.

Rao et al., "Role of the transsulfuration pathway and of gamma-cystathionase activity in the formation of cysteine and sulfate from methionine in rat hepatocytes," *J. Nutrition*, 120:837-845, 1990.

Response to Office Communication issued in U.S. Appl. No. 13/020,268, dated Oct. 9, 2013.

Sato and Nozaki, "Methionine gamma-lyase: the unique reaction mechanism, physiological roles, and therapeutic applications against infectious diseases and cancers," *IUMBM Life*, 61:1019-1028, 2009.

Schellenberger et al., "A recombinant polypeptide extends the in vivo half-life of peptides and proteins in a tunable manner," *Nat. Biotechnol.*, 27:1186-1190, 2009.

Sridhar et al., "Crystallization and preliminary crystallographic characterization of recombinant L-methionine-alpha-deamino-gamma-mercaptomethane lyase (methioninase)," *Acta. Crystall. Section D Biol. Crystall.*, 56:1665-1667, 2000.

Steegborn et al., "Kinetics and inhibition of recombinant human cystathionine gamma-lyase. Toward the rational control of trans-sulfuration," *J. Biol. Chem.*, 274:12675-12684, 1999.

Stone et al., "De novo engineering of a human cystathionine-γ-lyase for systemic (L)-Methionine depletion cancer therapy," *ACS Chem. Biol.*, 7(11):1822-1829, 2012.

Stone et al., "De novo engineering of a human cystathionine-γ-lyase for systemic (L)-Methionine depletion cancer therapy," *ACS Chem. Biol.*, 7(11):1822-1829, 2012. Supporting Information.

Stone et al., "Strategies for optimizing the serum persistence of engineered human arginase I for cancer therapy," *Journal of Controlled Release*, 158:171-179, 2012.

Sun et al., "In vivo efficacy of recombinant methioninase is enhanced by the combination of polyethylene glycol conjugation and pyridoxal 5'-phosphate supplementation," *Cancer Research*, 63:8377-8383, 2003.

Takakura et al., "Assay method for antitumor L-methionine-lyase: comprehensive kinetic analysis of the complex reaction with L-methionine." *Analytical Biochemistry*, 327(2):233-240, 2004.

Tan et al., "Anticancer efficacy of methioninase in vivo," *Anticancer Res.*, 16:3931-3936, 1996.

Tan et al., "Overexpression and large-scale production of recombinant L-methionine-alpha-deamino-gamma-mercaptomethane-lyase for novel anticancer therapy," *Protein Expr. Purif.*, 9:233-245, 1997.

Tan et al., "Recombinant methioninase infusion reduces the biochemical endpoint of serum methionine with minimal toxicity in high-stage cancer patients," *Anticancer Res.*, 17:3857-3860, 1997.

Tan et al., "Serum methionine depletion without side effects by methioninase in metastatic breast cancer patients," *Anticancer Res.*, 16:3937-3942, 1996.

Tiziani et al., "Metabolomics of the tumor microenvironment in pediatric acute lymphoblastic leukemia," *PLoS ONE*, 8:e82859, 2013.

Tiziani et al., "Optimized metabolite extraction from blood serum for 1H nuclear magnetic resonance spectroscopy," *Analytical Biochemistry*, 377:16-23, 2008.

(56) References Cited

OTHER PUBLICATIONS

Walter et al., "Strategies for the treatment of cystathionine beta-synthase deficiency: the experience of the Willink Biochemical Genetics Unit over the past 30 years," *European Journal of Pediatrics*, 157:S71-S76, 1998.

Wawrzynczak and Thorpe, In: *Immunoconjugates, Antibody Conjugates in Radioimaging and Therapy of Cancer*, Vogel (Ed.), NY, Oxford University Press, pp. 28-55, 1987.

Yan et al., "Structural Snapshots of an Engineered Cystathionine-[gamma]-lyase Reveal the Critical Role of the Electrostatic Interactions in the Active Site," *Biochemistry*, 56(6):876-885, 2017.

Yang et al., "PEGylation confers greatly extended half-life and attenuated immunogenicity to recombinant methioninase in primates," *Cancer Research*, 64:6673-6678, 2004.

Yang et al., "Pharmacokinetics, methionine depletion, and antigenicity of recombinant methioninase in primates," *Clinical Cancer Research*, 10:2131-2138, 2004.

Yoshioka et al., "Anticancer efficacy in vivo and in vitro, synergy with 5-fluorouracil, and safety of recombinant methioninase," *Cancer Res.*, 58:2583-2587, 1998.

Zhang et al., "Stromal control of cysteine metabolism promotes cancer cell survival in chronic lymphocytic leukemia," *Nat. Cell Biol.*, 14:276-286, 2012.

Zhao et al., "Frequent Epigenetic Silencing of the Folate-Metabolising Gene Cystathionine-Beta-Synthase in Gastrointestinal Cancer," *PLoS ONE*, 7(11):e49683, 2012.

Zhu et al., "Kinetic properties of polymorphic variants and pathogenic mutants in human cystathionine γ-lyase," *Biochemistry*, 47:6226-6232, 2008.

\* cited by examiner

```
SEQ ID NO: 1    1   MQEKDASSQGFLPHFQHFATQAIHVGQDPEQWTSRAVVPPISLSTTFKQGAPGQHSGFEYSRSGNPTRNCLEMAVAALDG   80
SEQ ID NO: 7    1   MQEKEASSQGFLPHFQHFATQAIHVGQEPEQWTSRAVVPPISPSVTFKQGAPGQHSGFVYSRSGNPTRNCLEKAVAALDG   80
SEQ ID NO: 8    1   MQEKDASSQGFLPHFQHFATQAIHVGQEPEQWTSRAVVPLISLSTTFKQAAPGQHSGFEYSRSGNPTRNCLEKAVAALDG   80
SEQ ID NO: 9    1   MQEKDASSQGFLPHFQHFATQAIHVGQDPEQWTSRALVPPISLSTTFKQGAPGQHSGFEYSRSGNPTRNCLEMAVAALDG   80
SEQ ID NO: 10   1   MQEKDASSQGFLPHFQHFATQAIHVGQDPEQWTSKALVPPISLSTTFKQGAPGQHSGFEYSRSGNPTRNCLEKAVAALDG   80

SEQ ID NO: 1    81  AKYCLAFASGLAATVTITHLLKAGDQIICMDDVYGGTNRYFRQVASEFGLNISFVDCSKIKLLEAAITPETKLVWIETPT  160
SEQ ID NO: 7    81  AKYCLAFASGLAATVTITHLLKAGDQIICMDDVYAGTNRYFRQVASEFGLKISFVDCSKIKLLEAAITPETKLVWIETPT  160
SEQ ID NO: 8    81  AKYCLAFASGLAATVTITHLLKAGDQIICMDDVYGGTNKYFRQVASEFGLKISFVDCSKIKLLEAAITPETKLVWIETPT  160
SEQ ID NO: 9    81  AKYCLAFASGLAATVTITHLLKAGDQIICMDDVYGGTNRYFRQVASEFGLKISFVDCSKIKLLEAAITPETKLVWIETPT  160
SEQ ID NO: 10   81  AKYCLAFASGLAATVTITHLLKAGDQIICMDDVYGGTNRYFRQVASEFGLKISFVDCSKIKLLEAAITPETKLVWIETPT  160

SEQ ID NO: 1    161 NPTQKVIDIESCAHIVHKHGDIILVVDNTFMSPYFQRPLALGADISMYSATKYMNGHSDVVMGLVSVNCESLHNRLRFLQ  240
SEQ ID NO: 7    161 NPTQFMTDIEACAHIVHKHGDIILVVDNTFMSPYFQRPLALGADICMCSATKYMNGHSDVVNGLVSVNCESLYNRLRFLQ  240
SEQ ID NO: 8    161 NPVLKHIDIEACAHIVHKRGDIILVVDNTFMSPYFQRPLALGADICHCSATKYHNGHSDVVMGLVSVNCERLHNRLRFLQ  240
SEQ ID NO: 9    161 NPTQKVIDIEACAHIVHKHGDIILVVDNTFMSPYFQRPLALGADICMYSATKYMNGHSDVVMGLVSVNCESLHNRLRFLQ  240
SEQ ID NO: 10   161 NPTQKVIDIEACAHIVHKHGDIILVLNTFMSPYFQRPLALGADICMYSATPYMNGHSDVVIGLVSVNCESLHNRLRFLQ   240

SEQ ID NO: 1    241 NSLGAVPSPIDCYLCNRGLKTLHVRMEKHFKNGMAVAQFLESNPWVEKVIYPGLPSHPQHELVKRQCTGCTGMVTFYIKG  320
SEQ ID NO: 7    241 NSLGAVPSPIDCYLCNRGLKTLQVRMEKHFKNGMAVAQFLESNPWVEKVIYPGLPSHPQHELVKRQCTGCTGMVTFYIKG  320
SEQ ID NO: 8    241 NSLGAVPSPIDCYLCNRGLKTLHVRMEKHFKNGMAVAQFLESNPGVEKVIYPGLPSHPQHELAKRQCTGCTGMIFFYIKG  320
SEQ ID NO: 9    241 NSLGAVPSPIDCYLCNRGLKTLHVRMEKHFKNGMAVAQFLESNPWVEKVIYPGLPSHPQHELVKRQCTGCTGMVTFYIKG  320
SEQ ID NO: 10   241 NSLGAVPSPIDCYLCNRGLKTLHVRMEKHFKNGMAVAQFLESNPWVEKVIYPGLPSHPQHELVKRQCTGCTGMVTFYIKG  320

SEQ ID NO: 1    321 TLQHAEIFLKNLKLFTLAESLGGFESLAELPAIMTHASVLKNDRDVLGISDTLIRLSVGLEDEEDLLEDLDQALKAAHPP  400
SEQ ID NO: 7    321 TLQHAEIFLKNLKLFTLAESLGGFESLVELPAVMTHASVLKKDRDVLGISDTLIRLSVGLEDEEDLLEDLDQALVAAHPP  400
SEQ ID NO: 8    321 TLQHAEIFLKNLKLFTLAESLGGFESLVELPAIMTHASVPKNDRDVLGISDTLIRLSVGLEDEKDLLEDLDQALKAAHPP  400
SEQ ID NO: 9    321 TLQHAEIFLKNLKLFTLAESLGGFESLAELPAIMTHASVLKNDRDVLGISDTLIRLSVGLEDEEDLLEDLDQALKAAHPP  400
SEQ ID NO: 10   321 TLQHAEIFLKNLKLFTLAESLGGFESLAELPAIMTHASVLNNDRDVLGISDTLIRLSVGLEDEEDLLEDLDQALNAAHPP  400

SEQ ID NO: 1    401 SGSHS  405
SEQ ID NO: 7    401 SGSHS  405
SEQ ID NO: 8    401 SGSHN  405
SEQ ID NO: 9    401 SGSHS  405
SEQ ID NO: 10   401 SGSHS  405
```

ENGINEERED PRIMATE CYSTINE/CYSTEINE DEGRADING ENZYMES FOR THERAPEUTIC USES

REFERENCE TO RELATED APPLICATIONS

The present application claims the priority benefit of U.S. provisional application No. 62/505,527, filed May 12, 2017, the entire contents of which is incorporated herein by reference.

STATEMENT REGARDING FEDERALLY SPONSORED RESEARCH

This invention was made with government support under Grant No. R01 CA189623 awarded by the National Institutes of Health. The government has certain rights in the invention.

REFERENCE TO A SEQUENCE LISTING

The instant application contains a Sequence Listing, which has been submitted in ASCII format via EFS-Web and is hereby incorporated by reference in its entirety. Said ASCII copy, created on May 9, 2018, is named UTSBP1123US_ST25.txt and is 57 kilobytes in size.

BACKGROUND

1. Field

Disclosed are recombinantly engineered primate enzyme variants having high cysteine/cysteine degrading activity and stability suitable for human therapy. Compositions and methods for the treatment of cancer and cystinuria with enzymes that deplete both L-cystine and L-cysteine are also provided.

2. Description of Related Art

Systemic depletion of various amino acids has been shown to be effective in killing a wide variety of tumor types with minimal toxicity to non-cancerous tissues. This therapeutic effect can be achieved through the use of pharmacologically optimized enzymes introduced into circulation that degrade the amino acid upon which the tumor relies. Certain cancers, such as prostate, small cell lung carcinomas, glioblastomas, and hepatocellular carcinomas, have been shown to be heavily dependent on extracellular cysteine/cystine in order to proliferate and survive. Many of these tumors aberrantly overexpress the xCT(−) cystine/glutamate antiporter (which is encoded by the SLC7A11 gene in humans) in order to maintain sufficient cysteine levels needed for protein and glutathione production, suggesting that they have lost or down-regulated their native cysteine biosynthetic capacity. In support of this idea, the use of small molecule inhibitors of xCT(−) cystine/glutamate antiporters, such as sulfasalazine, have been shown to retard the growth of prostate and small cell lung cancer tumor xenografts (Doxsee et al., 2007; Guan et al., 2009). Although a blockade of the xCT(−) dependent transport of L-cystine is promising it does not eliminate the transport of free L-cysteine by the Na$^+$ dependent ASC transporters and/or Na$^+$-independent transporters, and in some examples free L-cysteine is provided to tumor cells by bone-marrow derived stromal cells (Zhang et al., 2012). A therapeutic that depletes both cystine and cysteine can thus completely deprive tumors of this essential metabolite. However, there is a need for irreversible cysteine/cystine degrading enzymes with improved properties or activity suitable to be applied as human therapeutics.

SUMMARY

The present invention concerns the engineering of primate cystathionine-gamma-lyase ("CGL") enzymes such that both L-cystine and L-cysteine (referred to herein as "L-cyst(e)ine") can be efficiently degraded from serum, and providing the modified CGL enzymes in a formulation suitable for human therapy. To develop an enzyme displaying low $K_M$ and high catalytic activity, $k_{cat}$, as compared to the native enzyme, the native enzyme was engineered by modifying selected amino acids, which modifications result in an enzyme having dramatically improved enzymatic properties. As such, modified CGL enzymes, as described herein, overcome a major deficiency in the art by providing novel enzymes that comprise human or primate polypeptide sequences having improved L-cyst(e)ine-degrading catalytic activity. As this enzyme is comprised of a human sequence, it is not likely to induce adverse immunological responses. As such, these modified enzymes may be suitable for human therapy and have low immunogenicity and improved serum stability.

Methods are disclosed of utilizing an engineered human cystathionine-gamma-lyase (CGL) enzyme that efficiently converts cystine to cysteine-persulfide, which subsequently decays to free cysteine and $H_2S$, such that that it is a suitable therapy for treating cystinuria patients by preventing cystine accumulation and formation of stones in the kidney and urinary tract. As cystine is a non-essential amino acid, which is normally produced by most cells, no toxicities have been found to be induced by long-term cystine depletion in animal models. The ability of a cystine-degrading therapeutic to non-toxically ablate the total levels of circulating cystine indicate that it would be a superior therapeutic regimens for preventing cystine stone formation than existing therapeutic regimens.

Provided herein are modified CGL enzymes, having L-cyst(e)ine degrading activity, that are derived from primate CGL enzymes. A modified CGL enzyme may be derived from a human CGL enzyme (SEQ ID NO: 1), a *Pongo abelii* CGL enzyme (Genbank ID: NP_001124635.1; SEQ ID NO: 7), a *Macaca fascicularis* CGL enzyme (Genbank ID: AAW71993.1; SEQ ID NO: 8), a *Pan troglodytes* CGL enzyme (Genbank ID: XP_513486.2; SEQ ID NO: 9), or a *Pan paniscus* CGL enzyme (Genbank ID: XP_003830652.1; SEQ ID NO: 10). The native CGL enzyme may be modified by one or more other modifications, such as chemical modifications, substitutions, insertions, deletions, and/or truncations.

A modified CGL enzyme may be derived from a native, primate CGL enzyme by modifying by one, two, three, four or more substitutions at amino acid position 55, 59, 336, and/or 339 of SEQ ID NOs: 1 or 7-10. In these examples, the first methionine of each sequence corresponds to amino acid position 1, and each amino acid is numbered sequentially therefrom. The substitutions at amino acid positions 55, 59, and/or 339 may be glutamic acid (E), threonine (T), and valine (V), respectively. In addition, a modified CGL enzyme may comprise an additional substitution at amino acid position 336, said substitution being an aspartic acid (D)

A modified CGL enzyme may have an amino acid sequence according to SEQ ID NOs: 2-6 or 11-15. A modified CGL enzyme may be capable of degrading L-cyst(e)ine under physiological conditions. The modified CGL enzyme may have a catalytic efficiency for L-cyst(e)ine ($k_{cat}/K_M$) of at least or about 1000, 2000, 3000, 4000, 5000, 6000, 7000, 8000, 9000, $10^4$, $10^5$, $10^6$ $s^{-1}M^{-1}$ or any range derivable therein. An exemplary CGL enzyme may have a catalytic efficiency of >$10^4$ $s^{-1}M^{-1}$ for L-cystine and >$10^3$ $s^{-1}M^{-1}$ for L-cysteine.

The substitutions may be a combination of H55E, E59T, and E339V of human CGL (for example, the modified polypeptide having the amino acid sequence of SEQ ID NO: 2 or a fragment or homolog thereof). For example, an equivalent substitution of E59 in SEQ ID NO: 1 for SEQ ID NO: 7 would modify a valine and not glutamic acid as in SEQ ID NO: 1. The substitutions may be a combination of H55E, E59T, T336D, and E339V of human CGL (for example, the modified polypeptide having the amino acid sequence of SEQ ID NO: 11 or a fragment or homolog thereof). The modified polypeptide may be a *Pongo abelii* CGL-ETV mutant (SEQ ID NO: 3), *Macaca fascicularis* CGL-ETV mutant (SEQ ID NO: 4), *Pan troglodytes* CGL-ETV mutant (SEQ ID NO: 5), or *Pan paniscus* CGL-ETV mutant (SEQ ID NO: 6). The modified polypeptide may be a *Pongo abelii* CGL-ETDV mutant (SEQ ID NO: 12), *Macaca fascicularis* CGL-ETDV mutant (SEQ ID NO: 13), *Pan troglodytes* CGL-ETDV mutant (SEQ ID NO: 14), or *Pan paniscus* CGL-ETDV mutant (SEQ ID NO: 15).

A modified CGL enzyme as discussed herein may be characterized as having a certain percentage of identity as compared to an unmodified CGL enzyme (e.g., a native CGL enzyme). For example, the unmodified CGL enzyme may be a native primate cystathionase (i.e., cystathionine-γ-lyase). The percentage identity may be at least 90%, 95%, 96%, 97%, 98%, 99% or 100% (or any range derivable therein) between the unmodified portions of a modified CGL enzyme (i.e., the sequence of the modified CGL enzyme excluding any substitutions at amino acid positions 55, 59, 336, and/or 339 of SEQ ID NO: 1 or 7-10, see FIG. 1) and the native CGL enzyme. It is also contemplated that the percent identity discussed above may relate to a particular modified region of an enzyme as compared to an unmodified region of the corresponding native enzyme. For instance, a modified CGL enzyme may contain a modified or mutant substrate recognition site that can be characterized based on the identity of the amino acid sequence of the modified or mutant substrate recognition site to that of an unmodified or native CGL enzyme from the same species or across species. For example, a modified human CGL enzyme characterized as having at least 90% identity to an unmodified human CGL enzyme means that at least 90% of the amino acids in the modified human CGL enzyme are identical to the amino acids in the unmodified human CGL enzyme.

A modified CGL enzyme can be linked to a heterologous peptide sequence or polysaccharide. For example, a modified CGL enzyme may be linked to the heterologous peptide sequence as a fusion protein. The modified CGL enzyme may be linked to amino acid sequences, such as an IgG Fc, albumin, an albumin binding peptide, or an XTEN polypeptide for increasing the in vivo half-life. The modified CGL enzyme may be linked to a polysialic acid polymer.

To increase serum stability, the modified CGL enzyme may be linked to one or more polyether molecules. The polyether may be polyethylene glycol (PEG). The modified CGL enzyme may be linked to PEG via specific amino acid residues, such as lysine or cysteine. For therapeutic administration, such modified CGL enzyme may be dispersed in a pharmaceutically acceptable carrier.

A nucleic acid encoding a modified CGL enzyme is contemplated. The nucleic acid can be codon optimized for expression in bacteria, such as for *E. coli*. Nucleic acids that are codon optimized for the expression of the modified CGL enzymes provided in SEQ ID NOs: 2 and 11 in *E. coli* are provided in SEQ ID NOs: 16 and 17, respectively. Alternatively, the nucleic acid can be codon optimized for expression in fungus (e.g., yeast), insects, or mammals. Further contemplated are vectors, such as expression vectors, containing such nucleic acids. A nucleic acid encoding the modified CGL enzyme can be operably linked to a promoter, including but not limited to heterologous promoters. A modified CGL enzyme may be delivered to a target cell by a vector (e.g., a gene therapy vector). Such vectors may have been modified by recombinant DNA technology to enable the expression of the modified CGL-encoding nucleic acid in the target cell. These vectors may be derived from vectors of non-viral (e.g., plasmids) or viral (e.g., adenovirus, adeno-associated virus, retrovirus, lentivirus, herpes virus, or vaccinia virus) origin. Non-viral vectors may be complexed with agents to facilitate the entry of the DNA across the cellular membrane. Examples of such non-viral vector complexes include the formulation with polycationic agents, which facilitate the condensation of the DNA, and lipid-based delivery systems. Lipid-based delivery systems include liposome-based delivery of nucleic acids.

Host cells comprising such vectors are provided. The host cells may be bacteria (e.g., *E. coli*), fungal cells (e.g., yeast), insect cells, or mammalian cells.

A vector can be introduced into host cells for expressing the modified CGL enzyme. The modified CGL enzymes may be expressed in any suitable manner. The modified CGL enzymes may be expressed in a host cell such that the protein is glycosylated. Alternatively, the modified CGL enzymes may be expressed in a host cell such that the protein is aglycosylated.

Therapeutic formulations containing the modified CGL enzyme and a pharmaceutically acceptable carrier are provided. Therapeutic formulations can be administered intravenously, intradermally, intraarterially, intraperitoneally, intramuscularly, subcutaneously, by infusion, by continuous infusion, via a catheter, in lipid compositions (e.g., liposomes).

Methods are provided for treating a subject having a tumor cell (i.e., cancer) or having or being at risk of developing cystinuria comprising administering to the subject a therapeutically effective amount of a formulation comprising an isolated, modified primate CGL enzyme having at least one substitution relative to a native primate CGL amino acid sequence (see SEQ ID NOs: 1 and 7-10). Said at least one substitution includes a threonine at position 59. The modified enzyme may further include one or more of the following substitutions: a glutamic acid at position 55, an aspartic acid at position 336, and a valine at position 339 of the native primate CGL sequence or a nucleic acid comprising a nucleotide sequence encoding the isolated, modified primate CGL enzyme.

The subject may be any animal, such as a mouse. For example, the subject may be a mammal, a rodent, a primate, or a human patient. The subject or patient may be maintained on a L-cyst(e)ine-restricted diet, a methionine-restricted diet or a normal diet in combination with being treated with the described compositions.

The subject may have been previously been treated for cystinuria and the CGL enzyme is administered to treat or moderate the recurrence of cystinuria or ameliorate one or more conditions and/or symptoms associated with cystinuria. The methods may also comprise administering at least a second therapy to the subject, such as a second cystinuria therapy, such as modifications of diet, nutritional therapy, and shock wave therapy.

For patients having a cancer, the subject patient may have been previously treated for cancer and the CGL enzyme is administered to treat or moderate the cancer. The CGL enzyme may be coupled with a second therapy for cancer, which can include surgical therapy, chemotherapy, radiation therapy, cryotherapy, hormone therapy, immunotherapy, or cytokine therapy. The second anticancer therapy may be fludarabine.

The cancer may be any cancer that is sensitive to L-cyst(e)ine depletion. The cancer or the tumor cell may have been identified as having a decreased expression level of a cystathionine-β-synthase or cystathionine-γ-lyase gene product relative to a non-tumor cell. The cancer may be a prostate cancer, a small cell lung cancer, glioblastoma, hepatocellular cancer, pancreatic cancer, breast cancer, or a hematological malignancy, among others. The hematological malignancy cell may be a chronic myelogenous leukemia (CML) cell, chronic lymphocytic leukemia (CLL) cell, acute myelogenous leukemia (AML) cell, acute lymphocytic leukemia (ALL) cell, acute monocytic leukemia cell, diffuse large B-cell lymphoma, myelodysplastic syndrome, chronic myelomonocytic leukemia, primary myelofibrosis, Hodgkin's lymphoma cell, non-Hodgkin's lymphoma cell, or multiple myeloma cell.

Because tumor cells are dependent upon their nutrient medium for L-cyst(e)ine, the administration or treatment may be directed to the nutrient source for the cells, and not necessarily the cells themselves. Therefore, in an in vivo application, treating a tumor cell may comprise contacting the nutrient medium for a population of tumor cells with the engineered (i.e., modified) CGL enzyme. The medium can be blood, lymphatic fluid, spinal fluid and the like bodily fluid where L-cyst(e)ine depletion is desired.

A composition comprising a modified CGL enzyme or a nucleic acid encoding a modified CGL enzyme is provided for use in the treatment of cystinuria or cancer in a subject. The use of an isolated or modified CGL enzyme, a nucleic acid encoding a modified CGL enzyme, or a composition comprising said modified CGL enzyme in the manufacture of a medicament for therapeutic application to a cancer patient or cystinuria patient is provided. The modified CGL enzyme may be any modified CGL enzyme disclosed herein.

Also provided herein are:
1. An isolated, modified primate cystathionine-γ-lyase (CGL) enzyme having at least the following substitutions relative to a native human CGL amino acid sequence (SEQ ID NO: 1), wherein the modified enzyme has both cystinase and cysteinase activity, said substitutions comprising: a glutamic acid at position 55, a threonine at position 59, and a valine at position 339.
2. The isolated, modified CGL enzyme of claim 1, further comprising an aspartic acid at position 336.
3. The isolated, modified CGL enzyme of claim 1, wherein the isolated, modified CGL enzyme is a modified *Pongo abelii* CGL enzyme, wherein said substitutions comprise H55E, V59T, and E339V.
4. The isolated, modified CGL enzyme of claim 3, further comprising a T336D substitution.
5. The isolated, modified CGL enzyme of claim 1, wherein the isolated, modified CGL enzyme is a modified human CGL enzyme, a modified *Macaca fascicularis* CGL enzyme, a modified *Pan troglodytes* CGL enzyme, or a modified *Pan paniscus* CGL enzyme, wherein said substitutions comprise H55E, E59T, and E339V.
6. The isolated, modified CGL enzyme of claim 5, further comprising a T336D substitution.
7. The isolated, modified CGL enzyme of any one of claims 1-6, further comprising a heterologous peptide segment or a polysaccharide.
8. The isolated, modified CGL enzyme of claim 7, wherein the heterologous peptide segment is an XTEN peptide, an IgG Fc, an albumin, or an albumin binding peptide.
9. The isolated, modified CGL enzyme of claim 7, wherein the polysaccharide comprises polysialic acid polymers.
10. The isolated, modified CGL enzyme of any one of claims 1-9, wherein the enzyme is coupled to a polyethylene glycol (PEG).
11. The isolated, modified CGL enzyme of claim 10, wherein the enzyme is coupled to the PEG via one or more lysine residues.
12. A nucleic acid comprising a nucleotide sequence encoding the enzyme of any one of claims 1-6.
13. The nucleic acid of claim 12, wherein the nucleic acid is codon optimized for expression in bacteria, fungus, insects, or mammals.
14. The nucleic acid of claim 13, wherein the bacteria are *E. coli*.
15. The nucleic acid of claim 14, wherein the nucleic acid comprises SEQ ID NOs: 16 or 17.
16. An expression vector comprising the nucleic acid of any one of claims 12-15.
17. A host cell comprising the nucleic acid of any one of claims 12-15.
18. The host cell of claim 17, wherein the host cell is a bacterial cell, a fungal cell, an insect cell, or a mammalian cell.
19. A therapeutic formulation comprising an enzyme of any one of claims 1-11, or the nucleic acid of either claim 12 or 13, in a pharmaceutically acceptable carrier.
20. A method of treating a tumor cell or subject having a tumor cell comprising administering to the tumor cell or the subject a therapeutically effective amount of the formulation of claim 19.
21. The method of claim 20, wherein the subject is maintained on a L-cystine and/or L-cysteine restricted diet.
22. The method of claim 20, wherein the subject is maintained on a normal diet.
23. The method of claim 20, wherein the tumor cell has been identified as having a decreased expression level of a cystathionine-β-synthase or cystathionine-γ-lyase gene product relative to a non-tumor cell.
24. The method of claim 20, wherein the tumor cell has been identified as having an increased expression level of a xCT(−) cystine/glutamate antiporter gene product relative to a non-tumor cell.
25. The method of claim 20, wherein the tumor cell is a prostate cancer cells, a small cell lung cancer cell, or a hematological malignancy cell.
26. The method of claim 25, wherein the hematologic malignancy cell is a chronic myelogenous leukemia cell, chronic lymphocytic leukemia cell, acute myelogenous leukemia cell, acute lymphocytic leukemia cell, acute monocytic leukemia cell, diffuse large B-cell lymphoma, myelodysplastic syndrome, chronic myelomonocytic leukemia, primary myelofibrosis, Hodgkin's lymphoma cell, non-Hodgkin's lymphoma cell, or multiple myeloma cell.
27. The method of claim 20, wherein the subject is a human patient.

28. The method of claim 20, wherein the formulation is administered intravenously, intraarterially, intraperitoneally, intralesionally, intramuscularly, intravesicularlly, by injection, by infusion, by continuous infusion, by localized perfusion bathing target cells directly, or via a catheter.
29. The method of claim 20, wherein the formulation is administered to a nutrient medium of the tumor cell.
30. The method of claim 29, wherein the nutrient medium is blood, lymphatic fluid, or spinal fluid.
31. The method of claim 20, further comprising administering at least a second anticancer therapy to the subject.
32. The method of claim 31, wherein the second anticancer therapy is a surgical therapy, chemotherapy, radiation therapy, cryotherapy, hormone therapy, immunotherapy or cytokine therapy.
33. The method of claim 31, wherein the secondary anticancer therapy is fludarabine.
34. A method of treating a subject having or at risk of developing cystinuria comprising administering to the subject a therapeutically effective amount of a formulation of claim 19.
35. The method of claim 34, wherein the subject is maintained on a L-cystine and/or L-cysteine restricted diet.
36. The method of claim 34, wherein the subject is maintained on a methionine-restricted diet.
37. The method of claim 34, wherein the subject is maintained on a normal diet.
38. The method of claim 34, wherein the subject is a human patient.
39. The method of claim 34, wherein the formulation is administered intravenously, intraarterially, intraperitoneally, intramuscularly, intravascularly, subcutaneously, by injection, by infusion, by continuous infusion, by localized perfusion bathing target cells directly, or via a catheter.
40. The method of claim 34, wherein the subject has previously been treated for cystinuria and the enzyme is administered to prevent the recurrence of cystinuria.
41. The method of claim 34, further comprising administering at least a second cystinuria therapy to the subject.
42. The method of claim 41, wherein the second cystinuria therapy is a surgical therapy or a shock wave therapy.
43. Use of an isolated or modified CGL enzyme of any of claims 1 to 11 or a composition comprising said modified CGL enzyme for the manufacture of a medicament for therapeutic application to a cancer patient or a cystinuria patient.

As used herein the terms "encode" or "encoding," with reference to a nucleic acid, are used to make the invention readily understandable by the skilled artisan; however, these terms may be used interchangeably with "comprise" or "comprising," respectively.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

As used here, the term "about" is understood by persons of ordinary skill in the art and will vary to some extent on the context in which it is used. Generally, about encompasses a range of values that are plus/minus 10% of a referenced value.

BRIEF DESCRIPTION OF THE DRAWINGS

The following drawings form part of the present specification and are included to further exemplify the methods, compounds, and composition described.

FIG. 1—Sequence alignment of SEQ ID NOs: 1 and 7-10. Asterisks indicate engineered positions in various of the modified CGL enzymes.

DETAILED DESCRIPTION

Cysteine is considered a non-essential amino acid as it can be synthesized from homocysteine derived from the essential amino acid L-methionine via the transsulfuration pathway, which comprises the enzymes cystathionine-β-synthase (CBS) and cystathionine-γ-lyase (CGL). Thus, the depletion of L-cyst(e)ine is expected to be relatively non-toxic to normal tissues with an intact transsulfuration pathway. Provided are engineered, therapeutic enzymes that degrade L-cyst(e)ine at a lower $K_M$, potentially allowing for use of lower dosages. Also provided are methods of using said enzymes to treat diseases, such as cancer, a lysosomal storage disease (e.g., cystinosis), cystinuria, and to abrogate adverse immune effects in a variety of autoimmune conditions. Thus, a therapeutic enzyme that can deplete these amino acids may have utility as an immune modulating agent.

I. Definitions

As used herein the terms "enzyme" and "protein" and "polypeptide" refer to compounds comprising amino acids joined via peptide bonds and are used interchangeably.

As used herein, the term "fusion protein" refers to a chimeric protein containing proteins or protein fragments operably linked in a non-native way.

As used herein, the term "half-life" (½-life) refers to the time that would be required for the concentration of a polypeptide to fall by half in vitro (i.e., as measured in the cell culture media) or in vivo (i.e., as measured in serum), for example, after injection in a mammal. Methods to measure "half-life" include the use of antibodies specific for CGL or PEG used in an ELISA format such that the physical amount of protein is measured as a function of time. Other methods germane to measuring the half-life include determining the catalytic activity of the enzyme drug as a function of time by any assay that detects the production of any substrates resulting from conversion of L-cyst(e)ine, such as the detection of the reaction product pyruvate following derivatization with the agent 3-methyl-2-benzothiazolinone hydrazone (MBTH).

The terms "in operable combination," "in operable order," and "operably linked" refer to a linkage wherein the components so described are in a relationship permitting them to function in their intended manner, for example, a linkage of nucleic acid sequences in such a manner that a nucleic acid molecule capable of directing the transcription of a given gene and/or the synthesis of desired protein molecule, or a linkage of amino acid sequences in such a manner so that a fusion protein is produced.

The term "linker" is meant to refer to a compound or moiety that acts as a molecular bridge to operably link two different molecules, wherein one portion of the linker is operably linked to a first molecule, and wherein another portion of the linker is operably linked to a second molecule.

The term "PEGylated" refers to conjugation with polyethylene glycol (PEG), which has been widely used as a drug carrier, given its high degree of biocompatibility and ease of modification. PEG can be coupled (e.g., covalently linked) to active agents through the hydroxy groups at the end of the PEG chain via chemical methods; however, PEG itself is limited to at most two active agents per molecule. In a different approach, copolymers of PEG and amino acids have been explored as novel biomaterial that would retain the biocompatibility of PEG, but that would have the added advantage of numerous attachment points per molecule (thus providing greater drug loading), and that can be synthetically designed to suit a variety of applications.

The term "gene" refers to a DNA sequence that comprises control and coding sequences necessary for the production of a polypeptide or precursor thereof. The polypeptide can be encoded by a full-length coding sequence or by any portion of the coding sequence so as the desired enzymatic activity is retained.

The term "native" refers to the typical or wild-type form of a gene, a gene product, or a characteristic of that gene or gene product when isolated from a naturally occurring source. In contrast, the term "modified," "variant," "mutein," or "mutant" refers to a gene or gene product that displays modification in sequence and functional properties (i.e., altered characteristics) when compared to the native gene or gene product, wherein the modified gene or gene product is genetically engineered and not naturally present or occurring.

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques (see, for example, Maniatis et al., 1988 and Ausubel et al., 1994, both incorporated herein by reference).

The term "expression vector" refers to any type of genetic construct comprising a nucleic acid coding for an RNA capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host cell. In addition to control sequences that govern transcription and translation, vectors and expression vectors may contain nucleic acid sequences that serve other functions as well.

The term "therapeutically effective amount" as used herein refers to an amount of a therapeutic composition (i.e., a modified CGL enzyme or a nucleic acid encoding such an enzyme) that is employed in methods to achieve a therapeutic effect, i.e., to deplete L-cyst(e)ine in a patient's circulation to a level of about 0-15 µmol/L. The term "therapeutic benefit" or "therapeutically effective" as used throughout this application refers to anything that promotes or enhances the well-being of the subject with respect to the medical treatment of this condition. This includes, but is not limited to, a reduction in the frequency or severity of the signs or symptoms of a disease. For example, treatment of cystinuria may involve a reduction in the concentration of cystine in the urine, reduction in the size of a cystine stone, elimination of a cystine stone, or prevention of the formation of a cystine stone. For example, treatment of cancer may involve a reduction in tumor burden. The dosage ranges for the administration of therapeutic compositions are those large enough to produce the desired effect in which the symptoms of cystinuria or cancer are reduced. For example, a therapeutically effective amount of a therapeutic composition may be an amount such that when administered in a physiologically tolerable composition is sufficient to achieve an intravascular (plasma) concentration of from about 0.001 to about 100 units (U) per mL, preferably above about 0.1 U, and more preferably above 1 U modified CGL enzyme per mL. Typical dosages can be administered based on body weight, and are in the range of about 1-100 U/kilogram (kg)/day, preferably about 2-25 U/kg/day, and more preferably about 2-8 U/kg/day. An exemplary amount can be 5 U/kg/day or 35 U/kg/week. Normal human serum L-cyst(e)ine levels are around 200 µM. In the cystinuria patient, serum L-cyst(e)ine levels are reduced to around one half due to lack of renal cystine re-uptake, and dosages would be administered to obtain serum levels of L-cyst(e)ine of about 0-10 µM. In a cancer patient, dosages would be administered to obtain serum levels of L-cyst(e)ine of about 0-10 µM. The dosage should not be so large as to cause adverse side effects, such as hyperviscosity syndromes, pulmonary edema, congestive heart failure, and the like. Generally, the dosage will vary with age of, condition of, sex of, and extent of the disease in the patient and can be determined by one of skill in the art. The dosage can be adjusted by the individual physician in the event of any complication. The dosage should result in the L-cyst(e)ine content in a subject's serum being reduced at least by 50%, at least by 60%, and at least by 70% in about 12 to 24 hours. The dosage could result in the L-cyst(e)ine content in a subject's serum being reduced at least 50% to 70% in 6 hours.

The term "$K_M$" as used herein refers to the Michaelis-Menten constant for an enzyme and is defined as the concentration of the specific substrate at which a given enzyme yields one-half its maximum velocity in an enzyme catalyzed reaction. The term "$k_{cat}$" as used herein refers to the turnover number or the number of substrate molecules each enzyme site converts to product per unit time, and in which the enzyme is working at maximum efficiency. The term "$k_{cat}/K_M$" as used herein is the specificity constant, which is a measure of how efficiently an enzyme converts a substrate into product.

The term "cystathionine-γ-lyase" (CGL or cystathionase) refers to any enzyme that catalyzes the hydrolysis of cystathionine to cysteine. As used herein, the terms also contemplate primate forms of cystathionine-γ-lyase (or cystathionine-gamma-lyase), including the human form of cystathionine-γ-lyase.

"Treatment" and "treating" refer to administration or application of a therapeutic agent to a subject or performance of a procedure or modality on a subject to obtain a therapeutic benefit of a disease or health-related condition.

For example, treatment includes administration of a therapeutically effective amount of a modified CGL enzyme in order to reduce serum L-cyst(e)ine levels.

"Subject" and "patient" refer to either a human or a non-human, such as primates, mammals, and vertebrates.

II. Cystathionine-γ-lyase

A lyase is an enzyme that catalyzes the breaking of various chemical bonds, often forming a new double bond or a new ring structure. For example, an enzyme that catalyzed this reaction would be a lyase: ATP→cAMP+PP$_i$. Certain lyases only require one substrate; for example, cystathionine-γ-lyase converts L-cystathionine to L-cysteine, alpha-ketobutyrate, and ammonia. Other lyases, known as synthases, require two substrates; for example, cystathionine-β-synthase condenses serine and homocysteine to form cystathionine.

A number of pyrioxal-5'-phosphate (PLP)-dependent enzymes are involved in the metabolism of cysteine, homocysteine, and methionine, and these enzymes form an evolutionary related family, designated as Cysteine/Methionine (Cys/Met) metabolism PLP-dependent enzymes. These enzymes are proteins of about 400 amino acids and the PLP group forms an internal aldimine with a lysine residue located in the central location of the polypeptide. Members of this family include cystathionine-γ-lyase (CGL), cystathionine-γ-synthase (CGS), cystathionine-β-lyase (CBL), methionine-γ-lyase (MGL), and O-acetylhomoserine (OAH)/O-acetyl-serine (OAS) sulfhydrylase (OSHS). Common to all of the PLP-dependent enzymes is the formation of a Michaelis complex followed by transaldimination of the substrate leading to formation of an external aldimine. The further course of the reaction is determined by the substrate specificity of the particular enzyme.

For example, the inventors introduced specific mutations into a PLP-dependent lyase family member, cystathionine-γ-lyase, to change its substrate specificity. In this manner, variants were produced with the enhanced ability to degrade both L-cystine and L-cysteine. A modification of other PLP-dependent enzymes for producing novel L-cyst(e)ine degrading activity may also be contemplated.

CGL is a tetramer that catalyzes the last step in the mammalian transsulfuration pathway (Rao et al., 1990). CGL catalyzes the conversion of L-cystathionine to L-cysteine, alpha-ketobutyrate, and ammonia. Pyridoxal phosphate is a prosthetic group of this enzyme. Protein engineering was used to convert CGL, which has only weak activity for degrading L-cysteine and L-cystine, into an enzyme that can degrade L-cysteine and L-cystine at a high rate (U.S. Pat. No. 9,481,877, which is incorporated herein by reference in its entirety).

III. Cyst(e)inase Engineering

Due to the undesired effects of immunogenicity seen clinically with the use of non-human protein therapeutics, it is desirable to engineer therapeutically relevant L-cystine and L-cysteine degrading activity into a human enzyme (i.e., engineer a L-cyst(e)inase enzyme that displays high k$_{cat}$ and low K$_M$ values for both L-cystine and L-cysteine and also displaying a favorable specificity towards these two substrates). Humans have an enzyme called cystathionine-γ-lyase (hCGL) whose function is to catalyze the last step in the mammalian transsulfuration pathway (Rao et al., 1990), namely the conversion of L-cystathionine to L-cysteine, α-ketobutyrate, and ammonia. Human CGL can also weakly degrade L-cysteine and its disulfide form, L-cystine, making it an ideal candidate for engineering. Using structurally- and phylogenetically-guided mutagenesis, along with random mutagenesis approaches, hCGL variants were engineered to efficiently hydrolyze both L-cysteine and L-cystine.

Described are modified CGL enzymes that exhibits at least one functional activity that is comparable to the unmodified CGL enzyme. A modified CGL enzyme may be further modified to increase serum stability. Modified CGL enzymes include, for example, a protein that possesses an additional advantage, such as the cyst(e)inase enzyme activity, compared to the unmodified CGL enzyme. The unmodified protein or polypeptide may be a native cystathionine-γ-lyase, such as a human cystathionine-γ-lyase.

Determination of activity may be achieved using assays familiar to those of skill in the art, particularly with respect to the protein's activity, and may include for comparison purposes, for example, the use of native and/or recombinant versions of either the modified or unmodified enzymes. For example, wild-type human CGL slowly degrades L-cysteine to pyruvate, ammonia and H$_2$S, and converts L-cystine to pyruvate, ammonia, and thiocysteine (k$_{cat}$/K$_M$~0.2 s$^{-1}$ mM$^{-1}$ and ~0.8 s$^{-1}$ mM$^{-1}$, respectively). Thiocysteine is further nonenzymatically degraded to L-cysteine and H$_2$S. Thus, the L-cyst(e)ine degrading activity may be determined by any assay to detect the production of any substrates resulting from the degradation of L-cystine and/or L-cysteine, such as the detection of the reaction product pyruvate following derivatization with the agent 3-methyl-2-benzothiazolinone hydrazone (MBTH) (Takakura et al., 2004).

A modified CGL enzyme, may be identified based on its increase in L-cyst(e)ine degrading activity. For example, substrate recognition sites of the unmodified polypeptide may be identified. This identification may be based on structural analysis or homology analysis. A population of mutants involving modifications of such substrate recognitions sites may be generated. Mutants with increased L-cyst(e)ine degrading activity may be selected from the mutant population. Selection of desired mutants may include methods for the detection of byproducts or products from L-cyst(e)ine degradation.

Modified CGL enzymes may possess deletions and/or substitutions of amino acids; thus, an enzyme with a deletion, an enzyme with a substitution, and an enzyme with a deletion and a substitution are modified CGL enzymes. These modified CGL enzymes may further include insertions or added amino acids, such as with fusion proteins or proteins with linkers, for example. A "modified deleted CGL enzyme" lacks one or more residues of the native enzyme, but may possess the specificity and/or activity of the native enzyme. A modified deleted CGL enzyme may also have reduced immunogenicity or antigenicity. An example of a modified deleted CGL enzyme is one that has an amino acid residue deleted from at least one antigenic region, that is, a region of the enzyme determined to be antigenic in a particular organism, such as the type of organism that may be administered the modified CGL enzyme.

Substitution or replacement CGL enzyme variants may contain the exchange of one amino acid for another at one or more sites within the protein and may be designed to modulate one or more properties of the polypeptide, particularly its effector functions and/or bioavailability. Substitutions may or may not be conservative, that is, one amino acid is replaced with one of similar size and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine, or methionine; serine to threonine; threonine to serine; tryptophan to tyrosine; tyrosine to tryptophan or phenylalanine; and valine to isoleucine or leucine.

The term "biologically functional equivalent" is well understood in the art and is further defined in detail herein. Accordingly, CGL enzyme sequences that have about 90% or more sequence identity to SEQ ID NO: 1, or even between about 91% and about 99% of amino acids (including 92%, 93%, 94%, 95%, 96%, 97%, 98%, and 99%) that are identical to or conservative substitution of the amino acids of an modified CGL enzyme disclosed herein are included, provided the biological activity of the enzyme is maintained such that a measurable biological activity parameter (e.g., conversion of L-cystine and/or L-cysteine to pyruvate) is within about 20%, about 15%, about 10%, or about 5% of a modified CGL enzyme disclosed herein. A modified CGL enzyme may be biologically functionally equivalent to its unmodified counterpart.

Amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

One particular variant identified as having high catalytic activity for degrading both L-cystine and L-cysteine was found to have the following mutations: E59T, a synonymous codon change of R119R, and E339V. This variant is called hCGL-TV and was characterized for its ability to degrade L-cyst(e)ine in a 100 mM sodium phosphate buffer at pH 7.3 and 37° C. using a 1 mL scale MBTH assay similar to that described above. Under these conditions, the hCGL-TV variant was found to degrade L-cystine with a $k_{cat}$ of 2.6±0.01 s$^{-1}$, a K$_M$ of 0.06±0.01 mM, and a $k_{cat}$/K$_M$ of 43±7 s$^{-1}$ mM$^{-1}$. The hCGL-TV variant was further found to have a $k_{cat}$ of 1.7±0.05 s$^{-1}$, a K$_M$ of 0.33±0.03 mM, and a $k_{cat}$/K$_M$ of 5.1±0.5 s$^{-1}$ mM$^{-1}$ for degradation of L-cysteine. The hCGL-TV variant was found to have very high stability in human serum with an apparent T$_{0.5}$ of 228±6 h. In addition, the hCGL-TV was found to have an apparent IC$_{50}$ value of ~60 nM for both the DU145 and PC3 prostate tumor cell lines. In particular, two amino acid positions in addition to the two mutation sites (i.e. E59T-E339V) were found to confer improved activity compared to hCGL-TV. These additional positions are located at hCGL (SEQ ID NO: 1) residues 55 and 336 (see, FIG. 1). Mutation of one or more of these positions to H55E and T336D, in combination with substitution of residues at positions 59 and 339, resulted in improved activity compared to hCGL-TV. In particular, the variants contained amino acid substitutions corresponding to SEQ ID NO: 11, hCGL-H55E-E59T-T336D-E339V.

IV. Enzymatic L-cyst(e)ine Degradation for Therapy

Cysteine is considered a non-essential amino acid as it can be synthesized from homocysteine derived from the essential amino acid L-methionine via the transsulfuration pathway, which comprises the enzymes cystathionine-β-synthase (CBS) and cystathionine-γ-lyase (CGL). Thus, the depletion of cysteine is expected to be relatively non-toxic to normal tissues with an intact transsulfuration pathway.

The polypeptides may be used for the treatment of diseases, such as cystinuria or cancer, with novel enzymes that deplete L-cystine and/or L-cysteine. Disclosed are treatment methods using modified CGL with L-cyst(e)ine degrading activity. Enzymes with L-cyst(e)ine degrading activity for increased therapeutic efficacy are provided.

Provided are modified CGL enzymes with L-cyst(e)ine degrading activity for treating diseases, such as cytinuria and cancer. A modified polypeptide may have human polypeptide sequences and thus may prevent adverse immunogenic reactions when administered to human patients, allow repeated dosing, and increase the therapeutic efficacy.

As an example, PEG-hCGL-TV can drastically reduce serum cystine levels (>95%) for over 96 h and cysteine levels (80%) for over 48 h in a murine model. To determine this, male FVB/N mice of 6-7 weeks of age (JAX 001800) were injected intraperitoneally (i.p.) with 50 mg/kg of PEG-hCGL-TV and sacrificed at days 0, 1, 2, 4, and 6 (n=5 per group) for blood and serum collection. Serum samples were mixed with an internal standard mixture of 10 picomole deuterated cystine and cysteine and ultrafiltered using NANOSEP® OMEGA™ centrifugal devices, 3 kDa cutoff (Pall Life Biosciences) (Tiziani et al., 2008; Tiziani et al., 2013). The filtered polar fractions were chromatographed using a reverse-phase BEH C18, 1.7 μm, 2.1×150 mm column (THERMO SCIENTIFIC™ ACCELA® 1250 UPLC, Waters Corporation, USA) and introduced into an EXACTIVE™ Plus ORBITRAP™ mass spectrometer coupled with electrospray ionization (Thermo Fisher Scientific, San Jose, Calif.) according to manufacturer instructions. Data were acquired in centroid MS mode from 50 to 700 m/z mass range with the XCALIBUR™ software provided with instrument.

In addition, PEG-hCGL-TV demonstrated an absorption T$_{1/2}$ of approximately 23 h, and an elimination T$_{1/2}$ of 40±7 h. To determine this, a dot blot densitometry technique was used where appropriate serum samples were probed with an anti-hCGL antibody (rabbit anti-CTH Sigma # C8248) followed by addition of anti-rabbit IgG-fluorescein isothiocyanate (FITC) (Santa Cruz Biotechnology # sc-2012) and visualization by excitation at 488 nm on a TYPHOON™ scanner (GE Healthcare). Using ImageJ software (Schneider et al., 2012), densitometry of samples on the scanned dot blots were compared to titrations of known amounts of PEG-hCGL-TV within the same blot to construct a standard curve and calculate relative serum PEG-hCGL-TV levels. The data were fit to an extravascular model of administration (Foye et al., 2007).

Depletion can be conducted in vivo in the circulation of a mammal, in vitro in cases where L-cystine and/or L-cysteine depletion in tissue culture or other biological mediums is desired, and in ex vivo procedures where biological fluids, cells, or tissues are manipulated outside the body and subsequently returned to the body of the patient mammal. Depletion of L-cystine and/or L-cysteine from circulation, culture media, biological fluids, or cells is conducted to reduce the amount of L-cystine and/or L-cysteine accessible to the material being treated, and therefore comprises contacting the material to be depleted with a L-cystine- and/or L-cysteine-degrading amount of the engineered enzyme under L-cystine- and/or L-cysteine-degrading conditions as to degrade the ambient L-cystine and/or L-cysteine in the material being contacted.

L-cystine- and/or L-cysteine-degrading efficiency can vary widely depending upon the application, and typically depends upon the amount of L-cystine and/or L-cysteine present in the material, the desired rate of depletion, and the tolerance of the material for exposure to cyst(e)inase. L-cystine and/or L-cysteine levels in a material, and therefore rates of L-cystine and/or L-cysteine depletion from the material, can readily be monitored by a variety of chemical and biochemical methods well known in the art. Exemplary L-cystine- and/or L-cysteine-degrading amounts are described further herein, and can range from 0.001 to 100 units (U) of engineered cyst(e)inase, preferably about 0.01 to 10 U, and more preferably about 0.1 to 5 U engineered cyst(e)inase per milliliter (mL) of material to be treated.

L-cystine- and/or L-cysteine-degrading conditions are buffer and temperature conditions compatible with the biological activity of a CGL enzyme, and include moderate temperature, salt, and pH conditions compatible with the enzyme, for example, physiological conditions. Exemplary conditions include about 4-40° C., ionic strength equivalent to about 0.05 to 0.2 M NaCl, and a pH of about 5 to 9, while physiological conditions are included.

The contacting in vivo is accomplished by administering, by intravenous or intraperitoneal injection, a therapeutically effective amount of a physiologically tolerable composition comprising modified CGL enzyme to a patient, thereby depleting the circulating L-cystine and/or L-cysteine present in the patient.

The modified CGL enzyme can be administered parenterally by injection or by gradual infusion over time. The modified CGL enzyme can be administered intravenously, intraperitoneally, intramuscularly, subcutaneously, can be injected directly into the tissue containing the tumor cells, or can be administered by a pump connected to a catheter that may contain a potential biosensor for L-cyst(e)ine. For cystinuria, it may be desirable to administer the CGL enzymes subcutaneously.

The therapeutic compositions containing modified CGL enzyme are conventionally administered intravenously, as by injection of a unit dose, for example. The term "unit dose" when used in reference to a therapeutic composition refers to physically discrete units suitable as unitary dosage for the subject, each unit containing a predetermined quantity of active material calculated to produce the desired therapeutic effect in association with the required diluent, i.e., carrier, or vehicle.

The compositions are administered in a manner compatible with the dosage formulation, and in a therapeutically effective amount. The quantity to be administered depends on the subject to be treated, capacity of the subject's system to utilize the active ingredient, and degree of therapeutic effect desired. Precise amounts of active ingredient required to be administered depend on the judgment of the practitioner and are peculiar to each individual. However, suitable dosage ranges for systemic application are disclosed herein and depend on the route of administration. Suitable regimes for initial administration and booster shots are also contemplated and are typified by an initial administration followed by repeated doses at one or more hour intervals by a subsequent injection or other administration. Exemplary multiple administrations are described herein and are particularly preferred to maintain continuously high serum and tissue levels of modified CGL enzyme and conversely low serum and tissue levels of L-cyst(e)ine. Alternatively, continuous intravenous infusion sufficient to maintain concentrations in the blood in the ranges specified for in vivo therapies are contemplated.

A. Cystinuria

Cystinuria is a hereditary disorder caused by mutations in the SLC3A1 and SLC7A9 genes encoding the kidney proximal tubule's cystine and dibasic amino acid transporter that leads to abnormal excretion of cystine (the disulfide form of the amino acid cysteine) and the formation of cystine crystals/stones in the urinary tract due to low solubility of cystine.

Several mouse models of cystinuria are available, including a Slc7a9 knockout mouse, a Slc3a1 knockout mouse, a D140G Slc3a1 mutant mouse, and a E383K Slc3a1 mutant mouse (Feliubadalo et al., 2003; Ercolani et al., 2010; Peters et al., 2003; Livrozet et al., 2014, each of which is incorporated herein by reference in its entirety). Sequence analysis of Slc3a1 genomic DNA from 12952/SvPasCrl revealed a homozygous mutation in exon 7 in 12952/SvPasCrl mice. The A1232G point mutation is a missense mutation (c.1232G>A) in a highly conserved sequence. As a consequence of the A1232G missense mutation, the glutamine in position 383 is substituted for a lysine (E383K). This substitution stands in the extracellular part of rBAT and is responsible for the loss of rBAT expression and cystinuria in129S2/SvPasCrl mice (Livrozet et al., 2014). The glutamine in position 383 is highly conserved among various species.

Patients with cystinuria have a low quality of life, a life-long risk of cystine stone formation, impaired renal function and often require repeated surgical interventions. There are few therapeutics available to patients suffering from the hereditary disorder cystinuria wherein a defective kidney transporter is unable to re-uptake cystine during renal filtration. Cystine, the disulfide form of the amino acid L-cysteine, is highly insoluble and in cystinuria patients reaches high concentrations in the urinary tract resulting in the formation of cystine crystals and stones. Existing therapies that reduce circulating cystine levels partially prevent urinary tract stone formation but have significant adverse effects that limit their use.

There are no existing curative therapies for cystinuria and treatments are directed at increasing cystine solubility and lowering urinary cystine concentrations. Hyperdiuresis is a common treatment; however it requires daily consumption of >4 liters of water and urine volumes >3 liters which is difficult to achieve and maintain. Other drug treatments, such as small thiol molecules, function by reacting with cystine to form mixed disulfides that are more soluble than cystine but have significant toxicities, such as leukopenia, rash, fever, proteinuria and nephritic syndrome, which limit their use.

The present invention provides methods of using engineered, therapeutic enzymes that degrade L-cyst(e)ine to treat diseases, such as cystinuria. This method removes cystine from circulation, which has been shown clinically to reduce the incidence of kidney and urinary cystine stone formation in cystinuria patients. The method described here can reduce circulating cystine below detection levels without the side-effects associated with current cystinuria drugs.

B. Cancer

Certain cancers may have abnormally low or absent expression of transsulfuration pathway enzymes CBS and/or CGL. Since cysteine is a critical component of antioxidant pathways for tumor survival and treatment resistance, cancer cells are required to import L-cysteine/L-cystine from the extracellular compartment. In hepatocellular carcinomas, the downregulation of CBS was further correlated with poor prognosis (Kim et al., 2009), and gastrointestinal cancers have also been observed to have frequent epigenetic silencing of CBS (Zhao et al., 2012). In other examples, the absence of CGL expression has been frequently observed in lymphoblastic leukemia cell lines (Glode et al., 1981; Link et al., 1983). The expression levels of CBS and CGL, as well as the xCT(−) cysteine transporter, constitute tumor biomarkers for patient selection for treatment with a cystine/cysteine depletion regimen.

Hematological malignancies including Chronic Lymphocytic Leukemia (CLL), Acute Lymphocytic Leukemia (ALL), Acute Myeloid Leukemia (AML), Diffuse Large B-Cell Lymphoma (DLBCL), Myelodysplastic Syndrome (MDS), Chronic Myelomonocytic Leukemia (CMML), Primary Myelofibrosis (PMF), and Multiple Myeloma (MM) are dependent on the cellular antioxidant glutathione (GSH), consistent with the higher intrinsic oxidative stress. CLL and a subset of ALL cells have been reported to rely on the stromal supply of cysteine to increase the synthesis of GSH in order to maintain redox balance, which in turn promotes cell survival and fosters drug resistance. Beyond hematological malignancies, numerous other cancer cells require enhanced antioxidant mechanisms due to increased reactive oxygen species (ROS) levels arising from rapid proliferation, metabolic dysregulation, and oncogene expression. Consequently, the import of extracellular L-cyst(e)ine is required to meet cellular antioxidant demands in a multitude of malignancies including: the aforementioned hematological malignancies, glioblastomas, prostate, hepatocellular, pancreatic, and small cell lung carcinomas among others.

V. Conjugates

The compositions and methods provided involve further modification of the modified CGL enzyme for improvement, such as by forming conjugates with heterologous peptide segments or polymers, such as polyethylene glycol. The modified CGL enzyme may be linked to PEG to increase the hydrodynamic radius of the enzyme and hence increase the serum persistence or half-life. The disclosed polypeptide may be conjugated to any targeting agent, such as a ligand having the ability to specifically and stably bind to an external receptor or binding site on a tumor cell (U.S. Patent Publ. 2009/0304666). The PEG can be from about 3,000 to 20,000 Daltons in size, with an exemplary size being 5,000 Daltons.

A. Fusion Proteins

Fusion proteins are provided in which the modified CGL enzyme may be linked at the N- or C-terminus to a heterologous domain. For example, fusions may also employ leader sequences from other species to permit the recombinant expression of a protein in a heterologous host. Another useful fusion includes the addition of a protein affinity tag, such as a serum albumin affinity tag or six histidine residues, or an immunologically active domain, such as an antibody epitope, preferably cleavable, to facilitate purification of the fusion protein. Non-limiting affinity tags include polyhistidine, chitin binding protein (CBP), maltose binding protein (MBP), and glutathione-S-transferase (GST).

The modified CGL enzyme may be linked to a peptide that increases the in vivo half-life, such as an XTEN polypeptide (Schellenberger et al., 2009), IgG Fc domain, albumin, or an albumin binding peptide.

Methods of generating fusion proteins are well known to those of skill in the art. Such proteins can be produced, for example, by de novo synthesis of the complete fusion protein, or by attachment of the DNA sequence encoding the heterologous domain, followed by expression of the intact fusion protein.

Production of fusion proteins that recover the functional activities of the parent proteins may be facilitated by connecting genes with a bridging DNA segment encoding a peptide linker that is spliced between the polypeptides connected in tandem. The linker would be of sufficient length to allow proper folding of the resulting fusion protein.

B. Linkers

The modified CGL enzyme may be chemically conjugated using bifunctional cross-linking reagents or fused at the protein level with peptide linkers. Bifunctional cross-linking reagents have been extensively used for a variety of purposes, including preparation of affinity matrices, modification and stabilization of diverse structures, identification of ligand and receptor binding sites, and structural studies. Suitable peptide linkers may also be used to link the modified CGL enzyme, such as Gly-Ser linkers.

Homobifunctional reagents that carry two identical functional groups may induce cross-linking between identical and different macromolecules or subunits of a macromolecule, and link polypeptide ligands to their specific binding sites. Heterobifunctional reagents contain two different functional groups. By taking advantage of the differential reactivities of the two different functional groups, cross-linking can be controlled both selectively and sequentially. The bifunctional cross-linking reagents can be divided according to the specificity of their functional groups, e.g., amino-, sulfhydryl-, guanidine-, indole-, carboxyl-specific groups. Of these, reagents directed to free amino groups have become popular because of their commercial availability, ease of synthesis, and the mild reaction conditions under which they can be applied.

Some heterobifunctional cross-linking reagents contain a primary amine-reactive group and a thiol-reactive group. In another example, heterobifunctional cross-linking reagents and methods of using the cross-linking reagents are described (U.S. Pat. No. 5,889,155, specifically incorporated herein by reference in its entirety). The cross-linking reagents combine a nucleophilic hydrazide residue with an electrophilic maleimide residue, allowing coupling, in one example, of aldehydes to free thiols. The cross-linking reagent can be modified to cross-link various functional groups.

Additionally, any other linking/coupling agents and/or mechanisms known to those of skill in the art may be used to combine modified CGL enzymes, such as, for example, antibody-antigen interaction, avidin biotin linkages, amide linkages, ester linkages, thioester linkages, ether linkages, thioether linkages, phosphoester linkages, phosphoramide linkages, anhydride linkages, disulfide linkages, ionic and hydrophobic interactions, bispecific antibodies and antibody fragments, or combinations thereof.

It is preferred that a cross-linker having reasonable stability in blood will be employed. Numerous types of disulfide-bond containing linkers are known that can be successfully employed to conjugate targeting and therapeutic/preventative agents. Linkers that contain a disulfide bond that is sterically hindered may prove to give greater stability in vivo. These linkers are thus one group of linking agents.

In addition to hindered cross-linkers, non-hindered linkers also can be employed. Other useful cross-linkers, not considered to contain or generate a protected disulfide, include SATA, SPDP, and 2-iminothiolane (Wawrzynczak and Thorpe, 1987). The use of such cross-linkers is well understood in the art. Flexible linkers may also be used.

Once chemically conjugated, the peptide generally will be purified to separate the conjugate from unconjugated agents and from other contaminants. A large number of purification techniques are available for use in providing conjugates of a sufficient degree of purity to render them clinically useful.

Purification methods based upon size separation, such as gel filtration, gel permeation, or high performance liquid chromatography, will generally be of most use. Other chromatographic techniques, such as Blue-Sepharose separation, may also be used. Conventional methods to purify the fusion proteins from inclusion bodies may be useful, such as using weak detergents, such as sodium N-lauroyl-sarcosine (SLS).

C. PEGylation

Methods and compositions related to PEGylation of modified CGL enzyme are disclosed. For example, the modified CGL enzyme may be PEGylated in accordance with the methods disclosed herein.

PEGylation is the process of covalent attachment of poly(ethylene glycol) polymer chains to another molecule, normally a drug or therapeutic protein. PEGylation is routinely achieved by incubation of a reactive derivative of PEG with the target macromolecule. The covalent attachment of PEG to a drug or therapeutic protein can "mask" the agent from the host's immune system (reduced immunogenicity and antigenicity) or increase the hydrodynamic size (size in solution) of the agent, which prolongs its circulatory time by reducing renal clearance. PEGylation can also provide water solubility to hydrophobic drugs and proteins.

The first step of the PEGylation is the suitable functionalization of the PEG polymer at one or both terminals. PEGs that are activated at each terminus with the same reactive moiety are known as "homobifunctional," whereas if the functional groups present are different, then the PEG derivative is referred as "heterobifunctional" or "heterofunctional." The chemically active or activated derivatives of the PEG polymer are prepared to attach the PEG to the desired molecule.

The choice of the suitable functional group for the PEG derivative is based on the type of available reactive group on the molecule that will be coupled to the PEG. For proteins, typical reactive amino acids include lysine, cysteine, histidine, arginine, aspartic acid, glutamic acid, serine, threonine, and tyrosine. The N-terminal amino group and the C-terminal carboxylic acid can also be used.

The techniques used to form first generation PEG derivatives are generally reacting the PEG polymer with a group that is reactive with hydroxyl groups, typically anhydrides, acid chlorides, chloroformates, and carbonates.

As applications of PEGylation have become more and more advanced and sophisticated, there has been an increase in need for heterobifunctional PEGs for conjugation. These heterobifunctional PEGs are very useful in linking two entities, where a hydrophilic, flexible, and biocompatible spacer is needed. Preferred end groups for heterobifunctional PEGs can be maleimide, vinyl sulfones, pyridyl disulfide, amine, carboxylic acids, and NHS esters.

The most common modification agents, or linkers, are based on methoxy PEG (mPEG) molecules. Their activity depends on adding a protein-modifying group to the alcohol end. In some instances polyethylene glycol (PEG diol) is used as the precursor molecule. The diol is subsequently modified at both ends in order to make a hetero- or homodimeric PEG-linked molecule.

Proteins are generally PEGylated at nucleophilic sites, such as unprotonated thiols (cysteinyl residues) or amino groups. Examples of cysteinyl-specific modification reagents include PEG maleimide, PEG iodoacetate, PEG thiols, and PEG vinylsulfone. All four are strongly cysteinyl-specific under mild conditions and neutral to slightly alkaline pH but each has some drawbacks. The thioether formed with the maleimides can be somewhat unstable under alkaline conditions so there may be some limitation to formulation options with this linker. The carbamothioate linkage formed with iodo PEGs is more stable, but free iodine can modify tyrosine residues under some conditions. PEG thiols form disulfide bonds with protein thiols, but this linkage can also be unstable under alkaline conditions. PEG-vinylsulfone reactivity is relatively slow compared to maleimide and iodo PEG; however, the thioether linkage formed is quite stable. Its slower reaction rate also can make the PEG-vinylsulfone reaction easier to control.

Site-specific PEGylation at native cysteinyl residues is seldom carried out, since these residues are usually in the form of disulfide bonds or are required for biological activity. On the other hand, site-directed mutagenesis can be used to incorporate cysteinyl PEGylation sites for thiol-specific linkers. The cysteine mutation must be designed such that it is accessible to the PEGylation reagent and is still biologically active after PEGylation.

Amine-specific modification agents include PEG NHS ester, PEG tresylate, PEG aldehyde, PEG isothiocyanate, and several others. All react under mild conditions and are very specific for amino groups. The PEG NHS ester is probably one of the more reactive agents; however, its high reactivity can make the PEGylation reaction difficult to control on a large scale. PEG aldehyde forms an imine with the amino group, which is then reduced to a secondary amine with sodium cyanoborohydride. Unlike sodium borohydride, sodium cyanoborohydride will not reduce disulfide bonds. However, this chemical is highly toxic and must be handled cautiously, particularly at lower pH where it becomes volatile.

Due to the multiple lysine residues on most proteins, site-specific PEGylation can be a challenge. Fortunately, because these reagents react with unprotonated amino groups, it is possible to direct the PEGylation to lower-pK amino groups by performing the reaction at a lower pH. Generally, the pK of the alpha-amino group is 1-2 pH units lower than the epsilon-amino group of lysine residues. By PEGylating the molecule at pH 7 or below, high selectivity for the N-terminus frequently can be attained. However, this is only feasible if the N-terminal portion of the protein is not required for biological activity. Still, the pharmacokinetic benefits from PEGylation frequently outweigh a significant loss of in vitro bioactivity, resulting in a product with much greater in vivo bioactivity regardless of PEGylation chemistry.

There are several parameters to consider when developing a PEGylation procedure. Fortunately, there are usually no more than four or five parameters. The "design of experiments" approach to optimization of PEGylation conditions can be very useful. For thiol-specific PEGylation reactions, parameters to consider include: protein concentration, PEG-to-protein ratio (on a molar basis), temperature, pH, reaction time, and in some instances, the exclusion of oxygen. (Oxygen can contribute to intermolecular disulfide formation by the protein, which will reduce the yield of the PEGylated product.) The same factors should be considered (with the exception of oxygen) for amine-specific modification except that pH may be even more critical, particularly when targeting the N-terminal amino group.

For both amine- and thiol-specific modifications, the reaction conditions may affect the stability of the protein. This may limit the temperature, protein concentration, and pH. In addition, the reactivity of the PEG linker should be known before starting the PEGylation reaction. For example, if the PEGylation agent is only 70% active, the amount of PEG used should ensure that only active PEG molecules are counted in the protein-to-PEG reaction stoichiometry.

VI. Proteins and Peptides

Compositions comprising at least one protein or peptide, such as a modified CGL enzyme, are provided. These peptides may be comprised in a fusion protein or conjugated to an agent as described supra.

As used herein, a protein or peptide generally refers, but is not limited to, a protein of greater than about 200 amino acids, up to a full-length sequence translated from a gene; a polypeptide of greater than about 100 amino acids; and/or a peptide of from about 3 to about 100 amino acids. For convenience, the terms "protein," "polypeptide," and "peptide" are used interchangeably herein.

Accordingly, the term "protein or peptide" encompasses amino acid sequences comprising at least one of the 20 common amino acids found in naturally occurring proteins, or at least one modified or non-natural amino acid.

Proteins or peptides may be made by any technique known to those of skill in the art, including the expression of proteins, polypeptides, or peptides through standard molecular biological techniques, the isolation of proteins or peptides from natural sources, or the chemical synthesis of proteins or peptides. The coding regions for known genes may be amplified and/or expressed using the techniques disclosed herein or as would be known to those of ordinary skill in the art. Alternatively, various commercial preparations of proteins, polypeptides, and peptides are known to those of skill in the art.

VII. Nucleic Acids and Vectors

Nucleic acid sequences encoding a modified CGL enzyme or a fusion protein containing a modified CGL enzyme are disclosed. Depending on which expression system is used, nucleic acid sequences can be selected based on conventional methods. For example, if the modified CGL enzyme is derived from human cystathionase and contains multiple codons that are rarely utilized in *E. coli*, then that may interfere with expression. Therefore, the respective genes or variants thereof may be codon optimized for *E. coli* expression using freely available software (see Hoover & Lubkowski, 2002) to design coding sequences free of rare codons. Various vectors may be also used to express the protein of interest, such as a modified CGL enzyme. Exemplary vectors include, but are not limited, plasmid vectors, viral vectors, transposon, or liposome-based vectors.

VIII. Host Cells

Host cells may be any that may be transformed to allow the expression and secretion of modified CGL enzyme and conjugates thereof. The host cells may be bacteria, mammalian cells, yeast, or filamentous fungi. Various bacteria include *Escherichia* and *Bacillus*. Yeasts belonging to the genera *Saccharomyces, Kiuyveromyces, Hansenula*, or *Pichia* would find use as an appropriate host cell. Various species of filamentous fungi may be used as expression hosts, including the following genera: *Aspergillus, Trichoderma, Neurospora, Penicillium, Cephalosporium, Achlya, Podospora, Endothia, Mucor, Cochliobolus*, and *Pyricularia*.

Examples of usable host organisms include bacteria, e.g., *Escherichia coli* MC1061, derivatives of *Bacillus subtilis* BRB1 (Sibakov et al., 1984), *Staphylococcus aureus* SAI123 (Lordanescu, 1975) or *Streptococcus lividans* (Hopwood et al., 1985); yeasts, e.g., *Saccharomyces cerevisiae* AH 22 (Mellor et al., 1983) or *Schizosaccharomyces pombe*; and filamentous fungi, e.g., *Aspergillus nidulans, Aspergillus awamori* (Ward, 1989), or *Trichoderma reesei* (Penttila et al., 1987; Harkki et al., 1989).

Examples of mammalian host cells include Chinese hamster ovary cells (CHO-K1; American Type Culture Collection (ATCC) No. CCL61), rat pituitary cells (GH1; ATCC No. CCL82), HeLa S3 cells (ATCC No. CCL2.2), rat hepatoma cells (H-4-II-E; ATCC No. CRL-1548), SV40-transformed monkey kidney cells (COS-1; ATCC No. CRL-1650), and murine embryonic cells (NIH-3T3; ATCC No. CRL-1658). The foregoing is meant to be illustrative but not limitative of the many possible host organisms known in the art. In principle, all hosts capable of secretion can be used whether prokaryotic or eukaryotic.

Mammalian host cells expressing the modified CGL enzymes and/or their fusion proteins are cultured under conditions typically employed to culture the parental cell line. Generally, cells are cultured in a standard medium containing physiological salts and nutrients, such as standard RPMI, MEM, IMEM, or DMEM, typically supplemented with 5%-10% serum, such as fetal bovine serum or as described for the desired cell. Culture conditions are also standard, e.g., cultures are incubated at 37° C. in stationary or roller cultures until desired levels of the proteins are achieved.

IX. Protein Purification

Protein purification techniques are well known to those of skill in the art. These techniques involve, at one level, the homogenization and crude fractionation of the cells, tissue, or organ to polypeptide and non-polypeptide fractions. The protein or polypeptide of interest may be further purified using chromatographic and electrophoretic techniques to achieve partial or complete purification (or purification to homogeneity) unless otherwise specified. Analytical methods particularly suited to the preparation of a pure peptide are ion-exchange chromatography, gel exclusion chromatography, polyacrylamide gel electrophoresis, affinity chromatography, immunoaffinity chromatography, and isoelectric focusing. A particularly efficient method of purifying peptides is fast-performance liquid chromatography (FPLC) or even high-performance liquid chromatography (HPLC).

A purified protein or peptide is intended to refer to a composition, isolatable from other components, wherein the protein or peptide is purified to any degree relative to its naturally-obtainable state. An isolated or purified protein or peptide, therefore, also refers to a protein or peptide free from the environment in which it may naturally occur. Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95%, or more of the proteins in the composition.

Various techniques suitable for use in protein purification are well known to those of skill in the art. These include, for example, precipitation with ammonium sulfate, PEG, antibodies and the like, or by heat denaturation, followed by centrifugation; chromatography steps, such as ion exchange, gel filtration, reverse phase, hydroxyapatite, and affinity chromatography; isoelectric focusing; gel electrophoresis; and combinations of these and other techniques. As is generally known in the art, it is believed that the order of conducting the various purification steps may be changed, or that certain steps may be omitted, and still result in a suitable method for the preparation of a substantially purified protein or peptide.

Various methods for quantifying the degree of purification of the protein or peptide are known to those of skill in the art. These include, for example, determining the specific activity of an active fraction, or assessing the amount of polypeptides within a fraction by sodium dodecyl sulfate polyacrylamide gel electrophoresis (SDS/PAGE) analysis. A preferred method for assessing the purity of a fraction is to calculate the specific activity of the fraction, to compare it to the specific activity of the initial extract, and to thus calculate the degree of purity therein, assessed by a "-fold purification number." The actual units used to represent the amount of activity will, of course, be dependent upon the particular assay technique chosen to follow the purification, and whether or not the expressed protein or peptide exhibits a detectable activity.

There is no general requirement that the protein or peptide will always be provided in its most purified state. Indeed, it is contemplated that less substantially purified products may have utility. Partial purification may be accomplished by using fewer purification steps in combination, or by utilizing different forms of the same general purification scheme. For example, it is appreciated that a cation-exchange column chromatography performed utilizing a high-performance liquid chromatography (HPLC) apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

A protein or peptide may be isolated or purified, for example, a modified CGL enzyme, a fusion protein containing the modified CGL enzyme, or a modified CGL enzyme post PEGylation. For example, a His tag or an affinity epitope may be comprised in such a modified CGL enzyme to facilitate purification. Affinity chromatography is a chromatographic procedure that relies on the specific affinity between a substance to be isolated and a molecule to which it can specifically bind. This is a receptor-ligand type of interaction. The column material is synthesized by covalently coupling one of the binding partners to an insoluble matrix. The column material is then able to specifically adsorb the substance from the solution. Elution occurs by changing the conditions to those in which binding will not occur (e.g., altered pH, ionic strength, temperature, etc.). The matrix should be a substance that does not adsorb molecules to any significant extent and that has a broad range of chemical, physical, and thermal stability. The ligand should be coupled in such a way as to not affect its binding properties. The ligand should also provide relatively tight binding. It should be possible to elute the substance without destroying the sample or the ligand.

Size exclusion chromatography (SEC) is a chromatographic method in which molecules in solution are separated based on their size, or in more technical terms, their hydrodynamic volume. It is usually applied to large molecules or macromolecular complexes, such as proteins and industrial polymers. Typically, when an aqueous solution is used to transport the sample through the column, the technique is known as gel filtration chromatography, versus the name gel permeation chromatography, which is used when an organic solvent is used as a mobile phase.

The underlying principle of SEC is that particles of different sizes will elute (filter) through a stationary phase at different rates. This results in the separation of a solution of particles based on size. Provided that all the particles are loaded simultaneously or near simultaneously, particles of the same size should elute together. Each size exclusion column has a range of molecular weights that can be separated. The exclusion limit defines the molecular weight at the upper end of this range and is where molecules are too large to be trapped in the stationary phase. The permeation limit defines the molecular weight at the lower end of the range of separation and is where molecules of a small enough size can penetrate into the pores of the stationary phase completely and all molecules below this molecular mass are so small that they elute as a single band.

High-performance liquid chromatography (or high-pressure liquid chromatography, HPLC) is a form of column chromatography used frequently in biochemistry and analytical chemistry to separate, identify, and quantify compounds. HPLC utilizes a column that holds chromatographic packing material (stationary phase), a pump that moves the mobile phase(s) through the column, and a detector that shows the retention times of the molecules. Retention time varies depending on the interactions between the stationary phase, the molecules being analyzed, and the solvent(s) used.

X. Therapeutic Compositions

The human cystathionine-γ-lyase gene contains multiple codons that are rarely utilized in *E. coli* and can interfere with expression. Thus, in order to optimize protein expression in *E. coli*, the respective genes may be assembled with codon optimized oligonucleotides designed using DNA-Works software (Hoover et al., 2002). Each construct may contain an N-terminal NcoI restriction site, an in-frame N-terminal His$_6$ tag, and a C-terminal EcoRI site for simplifying cloning. After cloning into a pET28a vector (Novagen), *E. coli* (BL21) containing an appropriate modified CGL expression vector may be grown at 37° C. using Terrific Broth (TB) media containing 50 μg/mL kanamycin in shaker flasks at 250 rpm until reaching an OD$_{600}$ of ~0.5-0.6. At this point the cultures may be switched to a shaker at 25° C., induced with 0.5 mM IPTG, and allowed to express protein for an additional 12 h. Cell pellets may be then collected by centrifugation and re-suspended in an IMAC buffer (10 mM NaPO$_4$/10 mM imidazole/300 mM NaCl, pH 8). After lysis by means of a French pressure cell press or by a high pressure homogenizer, lysates may be centrifuged at 20,000×g for 20 min at 4° C., and the resulting supernatant applied to a nickel IMAC column (bead size 45-165 μm, Qiagen), washed extensively (90-100 column volumes) with an IMAC buffer containing 0.1% TRITON® 114, washed with 10-20 column volumes of IMAC buffer, and then eluted with an IMAC elution buffer (50 mM NaPO$_4$/250 mM imidazole/300 mM NaCl, pH 8). The purified protein was subjected to buffer exchange into a 100 mM NaPO$_4$ buffer at pH 8.3 using a 10,000 MWCO (molecule weight cut off) filtration device (Amicon). Fractions containing enzyme may be then incubated with 10 mM pyridoxal-5'-phosphate (PLP) for an hour at 25° C. Methoxy PEG succinimidyl carboxymethyl ester 5000 MW (JenKem Technology) was then added to modified CGL enzyme at an 80:1 molar ratio and allowed to react for 1 h at 25° C. under constant stirring. The resulting mixture was extensively buffer exchanged (PBS with 10% glycerol) using a 100,000 MWCO filtration device (Amicon), and sterilized with a 0.2 micron syringe filter (VWR). Enzyme aliquots may be then flash frozen in liquid nitrogen and stored at −80° C. The modified CGL enzyme variants purified in this manner should be >95% homogeneous as assessed by SDS-PAGE and Coomassie staining. The yield may be calculated based upon the calculated extinction coefficient, $\lambda_{280}$=29,870 M$^{-1}$ cm$^{-1}$ in a final buffer concentration of 6 M guanidinium hydrochloride, 20 mM phosphate buffer, pH 6.5 (Gill and von Hippel, 1989). PEGylated modified CGL enzymes may be analyzed for lipopolysaccharide (LPS) content using a Limulus Amebocyte Lysate (LAL) kit.

As an example, the serum stability of PEGylated modified CGL enzyme was tested by incubation of the enzyme in pooled human serum at 37° C. at a final concentration of 10 µM. At different time points, aliquots were withdrawn and tested for activity using the DTNB (Ellman's Reagent; 5,5-dithio-bis-(2-nitrobenzoic acid)) assay as described in U.S. Pat. Publ. 2011/0200576, which is incorporated herein by reference in its entirety. PEGylated modified CGL enzyme was calculated to have a half-life ($T_{0.5}$) of 101±4 h.

No limitation as to the particular nature of the therapeutic preparation is intended. For example, such compositions can be provided in formulations together with physiologically tolerable liquid, gel, or solid carriers, diluents, and excipients. These therapeutic preparations can be administered to mammals for veterinary use, such as with domestic animals, and clinical use in humans in a manner similar to other therapeutic agents. In general, the dosage required for therapeutic efficacy will vary according to the type of use and mode of administration, as well as the particularized requirements of individual subjects.

Such compositions are typically prepared as liquid solutions or suspensions, for use as injectables. Suitable diluents and excipients are, for example, water, saline, dextrose, glycerol, or the like, and combinations thereof. In addition, if desired, the compositions may contain minor amounts of auxiliary substances, such as wetting or emulsifying agents, stabilizing agents, or pH buffering agents.

Where clinical applications are contemplated, it may be necessary to prepare therapeutic compositions comprising proteins, antibodies, and drugs in a form appropriate for the intended application. Generally, therapeutic compositions may comprise an effective amount of one or more modified CGL enzymes or additional agents dissolved or dispersed in a pharmaceutically acceptable carrier. The phrases "therapeutic or therapeutically acceptable" refers to molecular entities and compositions that do not produce an adverse, allergic, or other untoward reaction when administered to an animal, such as, for example, a human, as appropriate. The preparation of a therapeutic composition that contains at least one modified CGL enzyme isolated by the method disclosed herein, or additional active ingredient will be known to those of skill in the art, as exemplified by Remington's Pharmaceutical Sciences, 18th Ed., 1990, incorporated herein by reference. Moreover, for animal (e.g., human) administration, it will be understood that preparations should meet sterility, pyrogenicity, general safety, and purity standards as required by the FDA Office of Biological Standards.

As used herein, "pharmaceutically acceptable carrier" includes any and all solvents, dispersion media, surfactants, antioxidants, preservatives (e.g., antibacterial agents, antifungal agents), isotonic agents, absorption delaying agents, salts, preservatives, drug stabilizers, gels, binders, excipients, such like materials and combinations thereof, as would be known to one of ordinary skill in the art (see, for example, Remington's Pharmaceutical Sciences, 18th Ed., 1990, incorporated herein by reference). Except insofar as any conventional carrier is incompatible with the active ingredient, its use in the therapeutic compositions is contemplated.

The compositions can be administered subcutaneously, intravenously, intraarterially, intraperitoneally, intramuscularly, by injection, by infusion, by continuous infusion, via a catheter, in lipid compositions (e.g., liposomes), or by other methods or any combination of the forgoing as would be known to one of ordinary skill in the art (see, for example, Remington's Pharmaceutical Sciences, 18th Ed., 1990, incorporated herein by reference).

The modified polypeptides may be formulated into a composition in a free base, neutral, or salt form. Therapeutically acceptable salts include the acid addition salts, e.g., those formed with the free amino groups of a proteinaceous composition, or which are formed with inorganic acids, such as, for example, hydrochloric or phosphoric acids, or such organic acids as acetic, oxalic, tartaric, or mandelic acid. Salts formed with the free carboxyl groups can also be derived from inorganic bases, such as, for example, sodium, potassium, ammonium, calcium, or ferric hydroxides; or such organic bases as isopropylamine, trimethylamine, histidine, or procaine. Upon formulation, solutions will be administered in a manner compatible with the dosage formulation and in such amount as is therapeutically effective. The formulations may be administered in a variety of dosage forms, such as being formulated for parenteral administrations, such as injectable solutions, or aerosols for delivery to the lungs, or formulated for alimentary administrations, such as drug release capsules and the like.

The disclosed compositions suitable for administration may be provided in a pharmaceutically acceptable carrier with or without an inert diluent. Except insofar as any conventional media, agent, diluent, or carrier is detrimental to the recipient or to the therapeutic effectiveness of the composition contained therein, its use in administrable composition for use in practicing the methods is appropriate. Examples of carriers or diluents include fats, oils, water, saline solutions, lipids, liposomes, and the like, or combinations thereof. The composition may also comprise various antioxidants to retard oxidation of one or more component. Additionally, the prevention of the action of microorganisms can be brought about by preservatives, such as various antibacterial and antifungal agents, including but not limited to parabens (e.g., methylparabens, propylparabens), chlorobutanol, phenol, sorbic acid, thimerosal or combinations thereof.

The disclosed compositions can be combined with the carrier in any convenient and practical manner, i.e., by solution, suspension, emulsification, admixture, encapsulation, absorption, and the like.

The actual dosage amount of a composition administered to an animal patient can be determined by physical and physiological factors, such as body weight, severity of condition, the type of disease being treated, previous or concurrent therapeutic interventions, idiopathy of the patient, and on the route of administration. Depending upon the dosage and the route of administration, the number of administrations of a preferred dosage and/or a therapeutically effective amount may vary according to the response of the subject. The practitioner responsible for administration will, in any event, determine the concentration of active ingredient(s) in a composition and appropriate dose(s) for the individual subject.

Therapeutic compositions may comprise, for example, at least about 0.1% of an active compound. An active compound may comprise between about 2% to about 75% of the weight of the unit, or between about 25% to about 60%, for example, and any range derivable therein. Naturally, the amount of active compound(s) in each therapeutically useful composition may be prepared in such a way that a suitable dosage will be obtained in any given unit dose of the compound. Factors, such as solubility, bioavailability, biological half-life, route of administration, product shelf life, as well as other pharmacological considerations, will be contemplated by one skilled in the art of preparing such therapeutic formulations, and as such, a variety of dosages and treatment regimens may be desirable.

A dose may also comprise from about 500 microgram/kg body weight, about 1 milligram/kg body weight, about 5 milligram/kg body weight, about 10 milligram/kg body weight, about 50 milligram/kg body weight, about 100 milligram/kg body weight, about 750 milligrams/kg body weight or more per administration, and any range derivable therein. If the dose is administered weekly, the dose could be in the amount of 5 mg/kg body weight, or for example 350 mg of protein for a 70 kg subject.

XI. Combination Treatments

The compositions and methods provided herein may involve administration of a modified CGL enzyme in combination with a second or additional therapy. Such therapy can be applied in the treatment of any disease that is associated with cyst(e)ine dependency. For example, the disease may be cystinuria or cancer.

Combination therapies may enhance the therapeutic or protective effect, and/or increase the therapeutic effect of another therapy. Therapeutic and prophylactic methods and compositions can be provided in a combined amount effective to achieve the desired effect, such as the elimination of cystine stones in the urinary tract or a decrease in tumor burden. This process may involve administering both a modified CGL enzyme and a second therapy. A tissue, organ, or cell can be exposed to one or more compositions or pharmacological formulation(s) comprising one or more of the agents (i.e., a modified CGL enzyme or a second agent), or by contacting the tissue, organ, and/or cell with two or more distinct compositions or formulations, wherein one composition provides 1) a modified CGL enzyme, 2) a second agent, or 3) both a modified CGL enzyme and a second agent. A combination therapy may be used in conjunction with shock wave therapy or surgical therapy.

The terms "contacted" and "exposed," when applied to a cell, are used herein to describe the process by which a therapeutic construct is delivered to a target organ or are placed in direct juxtaposition with the target cell. To achieve stone dissolution, for example, both agents are delivered to a cell in a combined amount effective to dissolve the stone or prevent it from forming or reforming.

A modified CGL enzyme may be administered before, during, after, or in various combinations relative to a second cystinuria or cancer treatment. The administrations may be in intervals ranging from concurrently to minutes to days to weeks. When the modified CGL enzyme is provided to a patient separately from a second cystinuria or cancer treatment, one would generally ensure that a significant period of time did not expire between the time of each delivery, such that the two treatments would still be able to exert an advantageously combined effect on the patient. In such instances, one may provide a patient with the modified CGL enzyme and the second cystinuria or cancer therapy within about 12 to 24 h or 72 h of each other or within about 6-12 h of each other. In some situations it may be desirable to extend the time period for treatment where several days (2, 3, 4, 5, 6, or 7) to several weeks (1, 2, 3, 4, 5, 6, 7, or 8) lapse between respective administrations.

For cancer, for example, a course of treatment may last 1-90 days or more (this such range includes intervening days). It is contemplated that the modified CGL may be given on any day of day 1 to day 90 (this such range includes intervening days) or any combination thereof, and another treatment may be given on any day of day 1 to day 90 (this such range includes intervening days) or any combination thereof. Within a single day (24-hour period), the patient may be given one or multiple administrations of the treatment(s). After a course of treatment, there may be a period of time at which no treatment is administered. This time period may last 1-7 days, and/or 1-5 weeks, and/or 1-12 months or more (this such range includes intervening days), depending on the condition of the patient, such as their prognosis, strength, health, etc. Treatment cycles can be repeated as necessary.

Various combinations may be employed. For the example below a modified CGL enzyme is "A" and a second cystinuria or cancer therapy is "B":

A/B/A B/A/B B/B/A A/A/B A/B/B B/A/A A/B/B/B B/A/B/B

B/B/B/A B/B/A/B A/A/B/B A/B/A/B A/B/B/A B/B/A/A

B/A/B/A B/A/A/B A/A/A/B B/A/A/A A/B/A/A A/A/B/A

Administration of any compound or therapy to a patient will follow general protocols for the administration of such compounds, taking into account the toxicity, if any, of the therapy. Therefore, there may be a step of monitoring toxicity that is attributable to the therapy.

A. Cystinuria Therapy

1. Surgery

One of the most common methods for the removal of cystine stones is percutaneous nephrolithotomy, in which a keyhole incision is made in the back and a nephroscope is used to break up and remove the stones. Although this procedure is less invasive than open surgery, regular or spinal anesthesia is normally required along with a hospital stay of 2 to 3 days and a recovery time of a few weeks.

2. Shock Wave Therapy

Cystinuric patients often have recurrent episodes of stone formation and surgeries in their lifetime. Shock wave lithotripsy, the use of high-energy shock waves for stone fragmentation, can be used for treatment of cystine stones that are smaller than 1.5 cm. Cystine stones are the sturdiest of all urinary stones and lithotripsy is generally ineffective in breaking them up. However, smaller cystine stones may be fragmented with lithotripsy because more frequent shocks at higher energy can be used.

3. Drug Therapy

Drug therapy for cystine stone related medical conditions involves the use of thiol-containing drugs, such as D-penicillamine, α-mercaptopropionylglycine (Thiola), and captopril, to break the cystine disulfide bond and form more soluble mixed disulfides or cysteine itself. However, these drugs frequently give the patient various unpleasant side effects, such as gastrointestinal intolerance, rash and joint pain (Sakhaee and Sutton, 1996).

4. Other Methods

Additional courses of treatment for removing cystine stones usually involve management of urinary cystine levels to reduce the risk of stone formation. These management methods include substantially increasing the intake of water (thereby increasing the urine volume and the amount of cystine that can be solubilized), dietary restrictions of sodium and methionine, which is a metabolic precursor of cystine, and oral administration of potassium citrate to increase the pH of the urine, thereby increasing the solubility of cystine.

An additional method for the treatment of cystine stones, which is a non-surgical and minimally invasive route, involves the delivery of chemical solutions to the kidneys via a nephrostomy catheter for the chemical dissolution of the stones, also known as chemodissolution. A variety of chemolytic agents have been used in this technique including sodium bicarbonate and the organic buffer tris-hydroxymethylene-aminomethane (tromethamine-E) at pH 10, both which act to provide a strongly alkaline environment to dissolve the cystine stones. Acetylcysteine is also frequently used in chemodissolution and dissolves the stones in a manner similar to D-penicillamine and Thiola by breaking the cystine disulfide and forming more soluble disulfides. However, this dissolution method has a limited role in the treatment of cystine stones because these chemolytic agents perform slowly and can typically take weeks to months to dissolve stones (Ng and Streem, 2001).

B. Cancer Therapy

1. Chemotherapy

A wide variety of chemotherapeutic agents may be used in accordance with the present invention. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyclosphosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antiobiotics (e.g., calicheamicin, especially calicheamicin gammaII and calicheamicin omegaI1); dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DFMO); retinoids, such as retinoic acid; capecitabine; carboplatin, procarbazine, plicomycin, gemcitabien, navelbine, farnesyl-protein tansferase inhibitors, transplatinum, and pharmaceutically acceptable salts, acids, or derivatives of any of the above.

2. Radiotherapy

Other factors that cause DNA damage and have been used extensively include what are commonly known as γ-rays, X-rays, and/or the directed delivery of radioisotopes to tumor cells. Other forms of DNA damaging factors are also contemplated, such as microwaves, proton beam irradiation (U.S. Pat. Nos. 5,760,395 and 4,870,287), and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

3. Immunotherapy

Immunotherapies may be used in combination or in conjunction with methods of the invention. In the context of cancer treatment, immunotherapeutics, generally, rely on the use of immune effector cells and molecules to target and destroy cancer cells. Rituximab (Rituxan®) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

The tumor cell might bear some marker that is amenable to targeting, i.e., is not present on the majority of other cells. Many tumor markers exist and any of these may be suitable for targeting in the context of the present invention. Common tumor markers include CD20, carcinoembryonic antigen, tyrosinase (p97), gp68, TAG-72, HMFG, Sialyl Lewis Antigen, MucA, MucB, PLAP, laminin receptor, erb B, and p155. Alternatively, anticancer effects may be combined with immune stimulatory effects. Immune stimulating molecules also exist including: cytokines, such as IL-2, IL-4, IL-12, GM-CSF, gamma-IFN, chemokines, such as MIP-1, MCP-1, IL-8, and growth factors, such as FLT3 ligand.

Examples of immunotherapies currently under investigation or in use are immune adjuvants, e.g., *Mycobacterium bovis, Plasmodium falciparum*, dinitrochlorobenzene, and aromatic compounds (U.S. Pat. Nos. 5,801,005 and 5,739, 169; Hui and Hashimoto, 1998; Christodoulides et al., 1998); cytokine therapy, e.g., interferons α, β, and γ, IL-1, GM-CSF, and TNF (Bukowski et al., 1998; Davidson et al., 1998; Hellstrand et al., 1998); gene therapy, e.g., TNF, IL-1, IL-2, and p53 (Qin et al., 1998; Austin-Ward and Villaseca, 1998; U.S. Pat. Nos. 5,830,880 and 5,846,945); and monoclonal antibodies, e.g., anti-CD20, anti-ganglioside GM2, and anti-p185 (Hollander, 2012; Hanibuchi et al., 1998; U.S. Pat. No. 5,824,311). It is contemplated that one or more anti-cancer therapies may be employed with the antibody therapies described herein.

4. Surgery

Surgery may include preventative, diagnostic or staging, curative, and palliative surgery. Curative surgery includes resection in which all or part of cancerous tissue is physically removed, excised, and/or destroyed and may be used in conjunction with other therapies, such as the treatment of the present invention, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

5. Other Agents

Other agents may be used in combination with the present invention to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions would increase the anti-hyperproliferative effects on the neighboring hyperproliferative cell population. Cytostatic or differentiation agents can be used in combination with the present invention to improve the anti-hyperproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. Other agents that increase the sensitivity of a hyperproliferative cell to apoptosis, such as the antibody c225, could be used in combination with the present invention to improve the treatment efficacy.

XII. Kits

Provided are kits, such as therapeutic kits. For example, a kit may comprise one or more therapeutic composition as described herein and optionally instructions for their use. Kits may also comprise one or more devices for accomplishing administration of such compositions. For example, a subject kit may comprise a therapeutic composition and catheter for accomplishing direct intravenous injection of the composition into a target tissue. A kit may comprise pre-filled ampoules of a modified CGL enzyme, optionally formulated as a therapeutic composition, or lyophilized, for use with a delivery device.

Kits may comprise a container with a label. Suitable containers include, for example, bottles, vials, and test tubes. The containers may be formed from a variety of materials, such as glass or plastic. The container may hold a composition that includes a modified CGL enzyme that is effective for therapeutic or non-therapeutic applications, such as described above. The label on the container may indicate that the composition is used for a specific therapy or non-therapeutic application, and may also indicate directions for either in vivo or in vitro use, such as those described above. Kits will typically comprise the container described above and one or more other containers comprising materials desirable from a commercial and user standpoint, including buffers, diluents, filters, needles, syringes, and package inserts with instructions for use.

XIII. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Characterization of Human Cyst(e)inease Variant hCGL-ETDV

To isolate optimized cyst(e)inase variants that have the requisites for clinical development, random and rational mutagenesis approaches coupled with a novel high-throughput screening strategy were sequentially employed. First, key amino acid substitutions that are crucial for enzymatic activity were identified by screening a comprehensive single-site saturation mutagenesis cyst(e)inase library generated by the PFunkel method (Firnberg and Ostermeier, 2012). Second, key residues identified during screening of the aforementioned cyst(e)inase PFunkel library were sequentially mutagenized using structural-based mutagenesis to develop variants that have improved biochemical properties. In the case that any CGL/cyst(e)inase variants introduced any new antigenic epitopes, these were then subjected to in silico analysis to identify any possible additional substitutions that may limit MHC class II binding peptides.

One particular variant identified through the mutagenesis approaches listed above as having the highest catalytic activity for degrading both L-cystine and L-cysteine was found to have the following mutations: H55E, E59T, T336D, and E339V. This variant was called hCGL-ETDV and was characterized for its ability to degrade L-cyst(e)ine in a 100 mM sodium phosphate buffer at pH 7.3 and 37° C. using a 1 mL scale MBTH assay similar to that described in Takakura et al., 2004.

Prophetic Example 2—Cytotoxicity of hCGL-ETDV in Combination with Fludarabine

The in vitro cytotoxicity of hCGL-ETDV will be assessed using patient-derived CLL samples. Cells will be seeded at and allowed to grow for 24 h before addition of either vehicle (control), 10 µM fludarabine, 0.2 µM hCGL-ETDV, or 0.2 µM hCGL-ETDV and 10 µM fludarabine in combination. After incubation for 48 hours, cell viability will be determined by flow cytometry after double staining of cells with Annexin-V-FITC and PI. Treatment with hCGL-ETDV alone or in combination with fludarabine is expected to decrease cell survival in a statistically significant manner relative to both vehicle and fludarabine alone.

The ability of PEG-hCGL-ETDV to improve survival will be evaluated in a transgenic murine model of CLL. Each of three treatment groups of mice will be administered either fludarabine (34 mg/kg QD×5 followed by 3 weeks respite until death), PEG-hCGL-ETDV (100 mg/kg bi-weekly until death), or PEG-hCGL-ETDV (100 mg/kg bi-weekly) and fludarabine (34 mg/kg QD×5 following by 3 weeks respite) in combination. A fourth group of mice will remain untreated as a control. The log-rank (Mantel-Cox) test will be used to analyze statistical significance for the Kaplan-Meier plots of mouse survival. Treatment with PEG-hCGL-ETDV alone or in combination with fludarabine is expected to improve survival in a statistically significant manner relative to both vehicle and fludarabine alone.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,870,287
U.S. Pat. No. 5,739,169
U.S. Pat. No. 5,760,395
U.S. Pat. No. 5,801,005
U.S. Pat. No. 5,824,311
U.S. Pat. No. 5,830,880
U.S. Pat. No. 5,846,945
U.S. Pat. No. 5,889,155
U.S. Pat. Publn. 2009/0304666
Austin-Ward and Villaseca, *Revista Medial de Chile*, 126(7): 838-845, 1998.
Ausubel et al., Current Protocols in Molecular Biology, Greene Publishing Associates and Wiley Interscience, N.Y., 1994.
Bukowski et al., *Clinical Cancer Res.*, 4(10): 2337-2347, 1998.
Christodoulides et al., *Microbiology*, 144(Pt 11): 3027-3037, 1998.
Davidson et al., *J. Immunother.*, 21(5): 389-398, 1998.
Doxsee et al., Sulfasalazine-induced cystine starvation: Potential use for prostate cancer therapy. *The Prostate*, 67(2): 162-171, 2007.
Ercolani et al., Bladder outlet obstruction in male cystinuria mice. *Int. Urol. Nephrol.* 42: 57-63, 2010.
Feliubadalo et al., Slc7a9-deficient mice develop cystinuria non-I and cystine urolithiasis. *Hum. Mol. Genet.*, 12: 2097-2108, 2003.
Foye et al., Foye's Principles of Medicinal Chemistry, Lippincott Williams & Wilkins, 2007.
Gill and von Hippel, Calculation of protein extinction coefficients from amino acid sequence data. *Anal. Biochem.*, 182(2): 319-326, 1989.
Glode et al., Cysteine auxotrophy of human leukemic lymphoblasts is associated with decreased amounts of intracellular cystathionase protein. *Biochemistry*, 20(5): 1306-1311, 1981.
Guan et al., The x c⁻ cystine/glutamate antiporter as a potential therapeutic target for small-cell lung cancer: use of sulfasalazine. *Cancer Chemotherapy and Pharmacology*, 64(3): 463-472, 2009.
Hanibuchi et al., *Int. J. Cancer*, 78(4): 480-485, 1998.
Harkki et al., *BioTechnology*, 7: 596-603, 1989.
Hellstrand et al., *Acta Oncologica*, 37(4): 347-353, 1998.
Hollander, *Front. Immun.*, 3:3, 2012.
Hopwood et al., In: *Genetic Manipulation of Streptomyces, A Laboratory Manual*, The John Innes Foundation, Norwich, Conn., 1985.
Hoover et al., The structure of human macrophage inflammatory protein-3alpha/CCL20. Linking antimicrobial and CC chemokine receptor-6-binding activities with human beta-defensins. *J. Biol. Chem.*, 277(40): 37647-37654, 2002.
Kim et al., Expression of cystathionine β-synthase is down-regulated in hepatocellular carcinoma and associated with poor prognosis. *Oncology Reports*, 21(6): 1449-1454, 2009.

Hui and Hashimoto, *Infection Immun.,* 66(11): 5329-5336, 1998.
Ito et al., *J. Biochem.,* 79: 1263, 1976.
Link et al., Cystathionase: a potential cytoplasmic marker of hematopoietic differentiation. *Blut,* 47(1): 31-39, 1983.
Livrozet et al., An animal model of Type A Cystinuria due to spontaneous mutation in 129S2/SvPasCrl Mice. *PLoS One* 9:e102700, 2014.
Lordanescu, *J. Bacteriol,* 12: 597-601, 1975.
Maniatis et al., Molecular Cloning, A Laboratory Manual, Cold Spring Harbor Press, Cold Spring Harbor, N.Y., 1988.
Mellor et al., *Gene,* 24: 1-14, 1983.
Penttila et al., *Gene,* 61: 155-164, 1987.
Peters et al., A mouse model for cystinuria type I. *Hum Mot Genet* 12: 2109-2120, 2003.
Qin et al., *Proc. Natl. Acad. Sci. USA,* 95(24): 14411-14416, 1998.
Rao et al., Role of the Transsulfuration Pathway and of {gamma}-Cystathionase Activity in the Formation of Cysteine and Sulfate from Methionine in Rat Hepatocytes. *Journal of Nutrition,* 120(8):837, 1990.
Remington's Pharmaceutical Sciences, 18th Ed. Mack Printing Company, 1289-1329, 1990.
Remington: The Science and Practice of Pharmacy, 22nd Ed. Pharmaceutical Press, 2013.
Schneider et al., 671 NIH image to imageJ: 25 years of image analysis. *Nature Methods,* 9:2012.
Sibakov et al., *Eur. J Biochem.,* 145: 567-572, 1984.
Stone et al., Strategies for optimizing the serum persistence of engineered human arginase I for cancer therapy. *Journal of Controlled Release,* 158:171-179, 2012.
Takakura et al., Assay method for antitumor L-methionine-lyase: comprehensive kinetic analysis of the complex reaction with L-methionine. *Analytical Biochemistry,* 327 (2): 233-240, 2004.
Tiziani et al., Optimized metabolite extraction from blood serum for 1H nuclear magnetic resonance spectroscopy. *Analytical Biochemistry,* 377: 16-23, 2008.
Tiziani et al., Metabolomics of the tumor microenvironment in pediatric acute lymphoblastic leukemia. *PLoS One,* 8:e82859, 2013.
Ward, Proc, Embo-Alko Workshop on Molecular Biology of Filamentous Fungi, Helsinki, 119-128, 1989.
Wawrzynczak and Thorpe, In: *Immunoconjugates, Antibody Conjugates In Radioimaging And Therapy Of Cancer,* Vogel (Ed.), NY, Oxford University Press, 28, 1987.
Zhang et al., Stromal control of cystine metabolism promotes cancer cell survival in chronic lymphocytic leukaemia. *Nature Cell Biology,* 14(3): 276-286, 2012.
Zhao et al., Frequent Epigenetic Silencing of the Folate-Metabolising Gene Cystathionine-Beta-Synthase in Gastrointestinal Cancer. *PLoS One,* 7(11): e49683, 2012.

What is claimed is:

1. An isolated, modified primate cystathionine-γ-lyase (CGL) enzyme having the following substitutions relative to a native human CGL amino acid sequence (SEQ ID NO: 1), wherein the modified enzyme has both cystinase and cysteinase activity, and wherein said primate is selected from the group consisting of Homo sapiens, Pongo abelii, Pan troglodytes, Pan paniscus, and Macaca fascicularis; said substitutions comprising: a glutamic acid at position 55, a threonine at position 59, and a valine at position 339.

2. The isolated, modified CGL enzyme of claim 1, further comprising an aspartic acid at position 336.

3. The isolated, modified CGL enzyme of claim 1, wherein the isolated, modified CGL enzyme is a modified Pongo abelii CGL enzyme, wherein said substitutions comprise H55E, V59T, and E339V.

4. The isolated, modified CGL enzyme of claim 3, further comprising a T336D substitution.

5. The isolated, modified CGL enzyme of claim 1, wherein the isolated, modified CGL enzyme is a modified Homo sapiens CGL enzyme, a modified Macaca fascicularis CGL enzyme, a modified Pan troglodytes CGL enzyme, or a modified Pan paniscus CGL enzyme, wherein said substitutions comprise H55E, E59T, and E339V.

6. The isolated, modified CGL enzyme of claim 5, further comprising a T336D substitution.

7. The isolated, modified CGL enzyme of claim 1, further comprising a heterologous peptide segment or a polysaccharide.

8. The isolated, modified CGL enzyme of claim 7, wherein the heterologous peptide segment is an XTEN peptide, an IgG Fc, an albumin, or an albumin binding peptide.

9. The isolated, modified CGL enzyme of claim 7, wherein the polysaccharide comprises polysialic acid polymers.

10. The isolated, modified CGL enzyme of claim 1, wherein the enzyme is coupled to a polyethylene glycol (PEG).

11. The isolated, modified CGL enzyme of claim 10, wherein the enzyme is coupled to the PEG via one or more lysine residues.

12. A therapeutic formulation comprising an enzyme of claim 1, in a pharmaceutically acceptable carrier.

13. A method of treating a tumor cell or subject having a tumor cell comprising administering to the tumor cell or the subject a therapeutically effective amount of the formulation of claim 12.

14. The method of claim 13, wherein the subject is maintained on a L-cystine and/or L-cysteine restricted diet.

15. The method of claim 13, wherein the subject is maintained on a normal diet.

16. The method of claim 13, wherein the tumor cell has been identified as having a decreased expression level of a cystathionine-β-synthase or cystathionine-γ-lyase gene product relative to a non-tumor cell.

17. The method of claim 13, wherein the tumor cell has been identified as having an increased expression level of a xCT(−) cystine/glutamate antiporter gene product relative to a non-tumor cell.

18. The method of claim 13, wherein the tumor cell is a prostate cancer cells, a small cell lung cancer cell, or a hematological malignancy cell.

19. The method of claim 18, wherein the hematologic malignancy cell is a chronic myelogenous leukemia cell, chronic lymphocytic leukemia cell, acute myelogenous leukemia cell, acute lymphocytic leukemia cell, acute monocytic leukemia cell, diffuse large B-cell lymphoma, myelodysplastic syndrome, chronic myelomonocytic leukemia, primary myelofibrosis, Hodgkin's lymphoma cell, non-Hodgkin's lymphoma cell, or multiple myeloma cell.

20. The method of claim 13, wherein the subject is a human patient.

21. The method of claim 13, wherein the formulation is administered intravenously, intraarterially, intraperitoneally, intralesionally, intramuscularly, intravesicularlly, by injection, by infusion, by continuous infusion, by localized perfusion bathing target cells directly, or via a catheter.

22. The method of claim 13, wherein the formulation is administered to a nutrient medium of the tumor cell.

23. The method of claim 22, wherein the nutrient medium is blood, lymphatic fluid, or spinal fluid.

24. The method of claim 13, further comprising administering at least a second anticancer therapy to the subject.

25. The method of claim 24, wherein the second anticancer therapy is a surgical therapy, chemotherapy, radiation therapy, cryotherapy, hormone therapy, immunotherapy or cytokine therapy.

26. The method of claim 24, wherein the secondary anticancer therapy is fludarabine.

27. A method of treating a subject having or at risk of developing cystinuria comprising administering to the subject a therapeutically effective amount of a formulation of claim 12.

28. The method of claim 27, wherein the subject is maintained on a L-cystine and/or L-cysteine restricted diet.

29. The method of claim 27, wherein the subject is maintained on a methionine-restricted diet.

30. The method of claim 27, wherein the subject is maintained on a normal diet.

31. The method of claim 27, wherein the subject is a human patient.

32. The method of claim 27, wherein the formulation is administered intravenously, intraarterially, intraperitoneally, intramuscularly, intravascularly, subcutaneously, by injection, by infusion, by continuous infusion, by localized perfusion bathing target cells directly, or via a catheter.

33. The method of claim 27, wherein the subject has previously been treated for cystinuria and the enzyme is administered to prevent the recurrence of cystinuria.

34. The method of claim 27, further comprising administering at least a second cystinuria therapy to the subject.

35. The method of claim 34, wherein the second cystinuria therapy is a surgical therapy or a shock wave therapy.

36. An isolated, modified human cystathionine-γ-lyase (CGL) enzyme having the following substitutions relative to a native human CGL amino acid sequence (SEQ ID NO: 1), wherein the modified enzyme has both cystinase and cysteinase activity, said substitutions comprising: a glutamic acid at position 55, a threonine at position 59, and a valine at position 339.

* * * * *

UNITED STATES PATENT AND TRADEMARK OFFICE
CERTIFICATE OF CORRECTION

PATENT NO. : 10,865,403 B2  
APPLICATION NO. : 15/977246  
DATED : December 15, 2020  
INVENTOR(S) : George Georgiou, Everett Stone and Shira Cramer Page 1 of 1

It is certified that error appears in the above-identified patent and that said Letters Patent is hereby corrected as shown below:

On the Title Page

Item (60), delete "Provisional application No. 62/055,527, filed on May 12, 2017." and replace with --Provisional application No. 62/505,527, filed on May 12, 2017.-- therefor.

Item (56) References Cited - Foreign Patent Documents, delete the 1st reference on page 2 "WO WO 2018/009663 1/1918" and replace with --WO WO 2018/009663 1/2018-- therefor.

Signed and Sealed this  
Third Day of August, 2021

Drew Hirshfeld  
*Performing the Functions and Duties of the*  
*Under Secretary of Commerce for Intellectual Property and*  
*Director of the United States Patent and Trademark Office*

SEQUENCE LISTING

```
<160> NUMBER OF SEQ ID NOS: 17

<210> SEQ ID NO 1
<211> LENGTH: 405
<212> TYPE: PRT
<213> ORGANISM: Homo sapiens

<400> SEQUENCE: 1

Met Gln Glu Lys Asp Ala Ser Ser Gln Gly Phe Leu Pro His Phe Gln
1               5                   10                  15

His Phe Ala Thr Gln Ala Ile His Val Gly Gln Asp Pro Glu Gln Trp
            20                  25                  30

Thr Ser Arg Ala Val Val Pro Pro Ile Ser Leu Ser Thr Thr Phe Lys
        35                  40                  45

Gln Gly Ala Pro Gly Gln His Ser Gly Phe Glu Tyr Ser Arg Ser Gly
    50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Leu Ala Ala Thr Val Thr
                85                  90                  95

Ile Thr His Leu Leu Lys Ala Gly Asp Gln Ile Ile Cys Met Asp Asp
            100                 105                 110

Val Tyr Gly Gly Thr Asn Arg Tyr Phe Arg Gln Val Ala Ser Glu Phe
        115                 120                 125

Gly Leu Lys Ile Ser Phe Val Asp Cys Ser Lys Ile Lys Leu Leu Glu
    130                 135                 140

Ala Ala Ile Thr Pro Glu Thr Lys Leu Val Trp Ile Glu Thr Pro Thr
145                 150                 155                 160

Asn Pro Thr Gln Lys Val Ile Asp Ile Glu Gly Cys Ala His Ile Val
                165                 170                 175

His Lys His Gly Asp Ile Ile Leu Val Val Asp Asn Thr Phe Met Ser
            180                 185                 190
```

Pro Tyr Phe Gln Arg Pro Leu Ala Leu Gly Ala Asp Ile Ser Met Tyr
            195                 200                 205

Ser Ala Thr Lys Tyr Met Asn Gly His Ser Asp Val Val Met Gly Leu
210                 215                 220

Val Ser Val Asn Cys Glu Ser Leu His Asn Arg Leu Arg Phe Leu Gln
225                 230                 235                 240

Asn Ser Leu Gly Ala Val Pro Ser Pro Ile Asp Cys Tyr Leu Cys Asn
            245                 250                 255

Arg Gly Leu Lys Thr Leu His Val Arg Met Glu Lys His Phe Lys Asn
            260                 265                 270

Gly Met Ala Val Ala Gln Phe Leu Glu Ser Asn Pro Trp Val Glu Lys
            275                 280                 285

Val Ile Tyr Pro Gly Leu Pro Ser His Pro Gln His Glu Leu Val Lys
            290                 295                 300

Arg Gln Cys Thr Gly Cys Thr Gly Met Val Thr Phe Tyr Ile Lys Gly
305                 310                 315                 320

Thr Leu Gln His Ala Glu Ile Phe Leu Lys Asn Leu Lys Leu Phe Thr
            325                 330                 335

Leu Ala Glu Ser Leu Gly Gly Phe Glu Ser Leu Ala Glu Leu Pro Ala
            340                 345                 350

Ile Met Thr His Ala Ser Val Leu Lys Asn Asp Arg Asp Val Leu Gly
            355                 360                 365

Ile Ser Asp Thr Leu Ile Arg Leu Ser Val Gly Leu Glu Asp Glu Glu
            370                 375                 380

Asp Leu Leu Glu Asp Leu Asp Gln Ala Leu Lys Ala Ala His Pro Pro
385                 390                 395                 400

Ser Gly Ser His Ser
            405

<210> SEQ ID NO 2
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 2

Met Gln Glu Lys Asp Ala Ser Ser Gln Gly Phe Leu Pro His Phe Gln
1               5                   10                  15

His Phe Ala Thr Gln Ala Ile His Val Gly Gln Asp Pro Glu Gln Trp
            20                  25                  30

Thr Ser Arg Ala Val Val Pro Pro Ile Ser Leu Ser Thr Thr Phe Lys
            35                  40                  45

Gln Gly Ala Pro Gly Gln Glu Ser Gly Phe Thr Tyr Ser Arg Ser Gly
            50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Leu Ala Ala Thr Val Thr
            85                  90                  95

Ile Thr His Leu Leu Lys Ala Gly Asp Gln Ile Ile Cys Met Asp Asp
            100                 105                 110

Val Tyr Gly Gly Thr Asn Arg Tyr Phe Arg Gln Val Ala Ser Glu Phe
            115                 120                 125

Gly Leu Lys Ile Ser Phe Val Asp Cys Ser Lys Ile Lys Leu Leu Glu
            130                 135                 140

Ala Ala Ile Thr Pro Glu Thr Lys Leu Val Trp Ile Glu Thr Pro Thr
145                 150                 155                 160

Asn Pro Thr Gln Lys Val Ile Asp Ile Glu Gly Cys Ala His Ile Val
            165                 170                 175

His Lys His Gly Asp Ile Ile Leu Val Val Asp Asn Thr Phe Met Ser
        180                 185                 190

Pro Tyr Phe Gln Arg Pro Leu Ala Leu Gly Ala Asp Ile Ser Met Tyr
    195                 200                 205

Ser Ala Thr Lys Tyr Met Asn Gly His Ser Asp Val Val Met Gly Leu
210                 215                 220

Val Ser Val Asn Cys Glu Ser Leu His Asn Arg Leu Arg Phe Leu Gln
225                 230                 235                 240

Asn Ser Leu Gly Ala Val Pro Ser Pro Ile Asp Cys Tyr Leu Cys Asn
                245                 250                 255

Arg Gly Leu Lys Thr Leu His Val Arg Met Glu Lys His Phe Lys Asn
            260                 265                 270

Gly Met Ala Val Ala Gln Phe Leu Glu Ser Asn Pro Trp Val Glu Lys
        275                 280                 285

Val Ile Tyr Pro Gly Leu Pro Ser His Pro Gln His Glu Leu Val Lys
    290                 295                 300

Arg Gln Cys Thr Gly Cys Thr Gly Met Val Thr Phe Tyr Ile Lys Gly
305                 310                 315                 320

Thr Leu Gln His Ala Glu Ile Phe Leu Lys Asn Leu Lys Leu Phe Thr
                325                 330                 335

Leu Ala Val Ser Leu Gly Gly Phe Glu Ser Leu Ala Glu Leu Pro Ala
            340                 345                 350

Ile Met Thr His Ala Ser Val Leu Lys Asn Asp Arg Asp Val Leu Gly
        355                 360                 365

Ile Ser Asp Thr Leu Ile Arg Leu Ser Val Gly Leu Glu Asp Glu Glu
    370                 375                 380

Asp Leu Leu Glu Asp Leu Asp Gln Ala Leu Lys Ala Ala His Pro Pro
385                 390                 395                 400

Ser Gly Ser His Ser
            405

<210> SEQ ID NO 3
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 3

Met Gln Glu Lys Glu Ala Ser Ser Gln Gly Phe Leu Pro His Phe Gln
1               5                   10                  15

His Phe Ala Thr Gln Ala Ile His Val Gly Gln Glu Pro Glu Gln Trp
            20                  25                  30

Thr Ser Arg Ala Val Val Pro Pro Ile Ser Pro Ser Val Thr Phe Lys
        35                  40                  45

Gln Gly Ala Pro Gly Gln Glu Ser Gly Phe Thr Tyr Ser Arg Ser Gly
    50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Leu Ala Ala Thr Val Thr
                85                  90                  95

```
Ile Thr His Leu Leu Lys Ala Gly Asp Gln Ile Ile Cys Met Asp Asp
            100                 105                 110

Val Tyr Ala Gly Thr Asn Arg Tyr Phe Arg Gln Val Ala Ser Glu Phe
            115                 120                 125

Gly Leu Lys Ile Ser Phe Val Asp Cys Ser Lys Ile Lys Leu Leu Glu
            130                 135                 140

Ala Ala Ile Thr Pro Glu Thr Lys Leu Val Trp Ile Glu Thr Pro Thr
145                 150                 155                 160

Asn Pro Thr Gln Lys Met Thr Asp Ile Glu Ala Cys Ala His Ile Val
                    165                 170                 175

His Lys His Gly Asp Ile Ile Leu Val Val Asp Asn Thr Phe Met Ser
            180                 185                 190

Pro Tyr Phe Gln Arg Pro Leu Ala Leu Gly Ala Asp Ile Cys Met Cys
            195                 200                 205

Ser Ala Thr Lys Tyr Met Asn Gly His Ser Asp Val Val Met Gly Leu
            210                 215                 220

Val Ser Val Asn Cys Glu Ser Leu Tyr Asn Arg Leu Arg Phe Leu Gln
225                 230                 235                 240

Asn Ser Leu Gly Ala Val Pro Ser Pro Ile Asp Cys Tyr Leu Cys Asn
                    245                 250                 255

Arg Gly Leu Lys Thr Leu Gln Val Arg Met Glu Lys His Phe Lys Asn
            260                 265                 270

Gly Met Ala Val Ala Gln Phe Leu Glu Ser Asn Pro Trp Val Glu Lys
            275                 280                 285

Val Ile Tyr Pro Gly Leu Pro Ser His Pro Gln His Glu Leu Val Lys
            290                 295                 300

Arg Gln Cys Thr Gly Cys Thr Gly Met Val Thr Phe Tyr Ile Lys Gly
305                 310                 315                 320

Thr Leu Gln His Ala Glu Ile Phe Leu Lys Asn Leu Lys Leu Phe Thr
                    325                 330                 335

Leu Ala Val Ser Leu Gly Gly Phe Glu Ser Leu Val Glu Leu Pro Ala
            340                 345                 350

Val Met Thr His Ala Ser Val Leu Lys Lys Asp Arg Asp Val Leu Gly
            355                 360                 365

Ile Ser Asp Thr Leu Ile Arg Leu Ser Val Gly Leu Glu Asp Glu Glu
            370                 375                 380

Asp Leu Leu Glu Asp Leu Asp Gln Ala Leu Lys Ala Ala His Pro Pro
385                 390                 395                 400

Ser Gly Ser His Ser
            405

<210> SEQ ID NO 4
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 4

Met Gln Glu Lys Asp Ala Ser Ser Gln Gly Phe Leu Pro His Phe Gln
1               5                   10                  15

His Phe Ala Thr Gln Ala Ile His Val Gly Gln Glu Pro Glu Gln Trp
            20                  25                  30

Thr Ser Arg Ala Val Val Pro Leu Ile Ser Leu Ser Thr Thr Phe Lys
            35                  40                  45
```

Gln Ala Ala Pro Gly Gln Glu Ser Gly Phe Thr Tyr Ser Arg Ser Gly
 50                  55                  60

Asn Pro Thr Arg Asn Cys Leu Glu Lys Ala Val Ala Ala Leu Asp Gly
 65                  70                  75                  80

Ala Lys Tyr Cys Leu Ala Phe Ala Ser Gly Leu Ala Ala Thr Val Thr
                 85                  90                  95

Ile Thr His Leu Leu Lys Ala Gly Asp Gln Ile Ile Cys Met Asp Asp
                100                 105                 110

Val Tyr Gly Gly Thr Asn Arg Tyr Phe Arg Gln Val Ala Ser Glu Phe
            115                 120                 125

Gly Leu Lys Ile Ser Phe Val Asp Cys Ser Lys Ile Lys Leu Leu Glu
    130                 135                 140

Ala Ala Ile Thr Pro Glu Thr Lys Leu Val Trp Ile Glu Thr Pro Thr
145                 150                 155                 160

Asn Pro Val Leu Lys Met Ile Asp Ile Glu Ala Cys Ala His Ile Val
                165                 170                 175

His Lys Arg Gly Asp Ile Ile Leu Val Val Asp Asn Thr Phe Met Ser
            180                 185                 190

Pro Tyr Phe Gln Arg Pro Leu Ala Leu Gly Ala Asp Ile Cys Met Cys
        195                 200                 205

Ser Ala Thr Lys Tyr Met Asn Gly His Ser Asp Val Val Met Gly Leu
    210                 215                 220

Val Ser Val Asn Cys Glu Arg Leu His Asn Arg Leu Arg Phe Leu Gln
225                 230                 235                 240

Asn Ser Leu Gly Ala Val Pro Ser Pro Leu Asp Cys Tyr Leu Cys Asn
                245                 250                 255

Arg Gly Leu Lys Thr Leu His Val Arg Met Glu Lys His Phe Lys Asn
            260                 265                 270

Gly Met Ala Val Ala Gln Phe Leu Glu Ser Asn Pro Gly Val Glu Lys
        275                 280                 285

Val Ile Tyr Pro Gly Leu Pro Ser His Pro Gln His Glu Leu Ala Lys
    290                 295                 300

Arg Gln Cys Thr Gly Cys Thr Gly Met Ile Thr Phe Tyr Ile Lys Gly
305                 310                 315                 320

Thr Leu Gln His Ala Glu Ile Phe Leu Lys Asn Leu Lys Leu Phe Thr
                325                 330                 335

Leu Ala Val Ser Leu Gly Gly Phe Glu Ser Leu Val Glu Leu Pro Ala
            340                 345                 350

Ile Met Thr His Ala Ser Val Pro Lys Asn Asp Arg Asp Val Leu Gly
        355                 360                 365

Ile Ser Asp Thr Leu Ile Arg Leu Ser Val Gly Leu Glu Asp Glu Lys
    370                 375                 380

Asp Leu Leu Glu Asp Leu Asp Gln Ala Leu Lys Ala Ala His Pro Pro
385                 390                 395                 400

Ser Gly Ser His Asn
                405

<210> SEQ ID NO 5
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 5

```
Met Gln Glu Lys Asp Ala Ser Ser Gln Gly Phe Leu Pro His Phe Gln
1               5                  10                 15

His Phe Ala Thr Gln Ala Ile His Val Gly Gln Asp Pro Glu Gln Trp
            20                  25                 30

Thr Ser Arg Ala Leu Val Pro Pro Ile Ser Leu Ser Thr Thr Phe Lys
        35                  40                 45

Gln Gly Ala Pro Gly Gln Glu Ser Gly Phe Thr Tyr Ser Arg Ser Gly
    50                  55                 60

Asn Pro Thr Arg Asn Cys Leu Glu Lys Ala Val Ala Ala Leu Asp Gly
65                  70                 75                 80

Ala Lys Tyr Cys Leu Ala Phe Ala Ser Gly Leu Ala Ala Thr Val Thr
                85                  90                 95

Ile Thr His Leu Leu Lys Ala Gly Asp Gln Ile Ile Cys Met Asp Asp
                100                 105                110

Val Tyr Gly Gly Thr Asn Arg Tyr Phe Arg Gln Val Ala Ser Glu Phe
            115                 120                125

Gly Leu Lys Ile Ser Phe Val Asp Cys Ser Lys Ile Lys Leu Leu Glu
        130                 135                140

Ala Ala Ile Thr Pro Glu Thr Lys Leu Val Trp Ile Glu Thr Pro Thr
145                 150                 155                160

Asn Pro Thr Gln Lys Val Ile Asp Ile Glu Ala Cys Ala His Ile Val
                165                 170                175

His Lys His Gly Asp Ile Ile Leu Val Val Asp Asn Thr Phe Met Ser
            180                 185                 190

Pro Tyr Phe Gln Arg Pro Leu Ala Leu Gly Ala Asp Ile Cys Met Tyr
        195                 200                 205

Ser Ala Thr Lys Tyr Met Asn Gly His Ser Asp Val Val Met Gly Leu
    210                 215                 220

Val Ser Val Asn Cys Glu Ser Leu His Asn Arg Leu Arg Phe Leu Gln
225                 230                 235                 240

Asn Ser Leu Gly Ala Val Pro Ser Pro Ile Asp Cys Tyr Leu Cys Asn
                245                 250                 255

Arg Gly Leu Lys Thr Leu His Val Arg Met Glu Lys His Phe Lys Asn
            260                 265                 270

Gly Met Ala Val Ala Gln Phe Leu Glu Ser Asn Pro Trp Val Glu Lys
        275                 280                 285

Val Ile Tyr Pro Gly Leu Pro Ser His Pro Gln His Glu Leu Val Lys
    290                 295                 300

Arg Gln Cys Thr Gly Cys Thr Gly Met Val Thr Phe Tyr Ile Lys Gly
305                 310                 315                 320

Thr Leu Gln His Ala Glu Ile Phe Leu Lys Asn Leu Lys Leu Phe Thr
                325                 330                 335

Leu Ala Val Ser Leu Gly Gly Phe Glu Ser Leu Ala Glu Leu Pro Ala
            340                 345                 350

Ile Met Thr His Ala Ser Val Leu Lys Asn Asp Arg Asp Val Leu Gly
        355                 360                 365

Ile Ser Asp Thr Leu Ile Arg Leu Ser Val Gly Leu Glu Asp Glu Glu
    370                 375                 380

Asp Leu Leu Glu Asp Leu Asp Gln Ala Leu Lys Ala Ala His Pro Pro
385                 390                 395                 400

Ser Gly Ser His Ser
            405
```

<210> SEQ ID NO 6
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 6

```
Met Gln Glu Lys Asp Ala Ser Ser Gln Gly Phe Leu Pro His Phe Gln
1               5                   10                  15

His Phe Ala Thr Gln Ala Ile His Val Gly Gln Asp Pro Glu Gln Trp
            20                  25                  30

Thr Ser Lys Ala Leu Val Pro Pro Ile Ser Leu Ser Thr Thr Phe Lys
        35                  40                  45

Gln Gly Ala Pro Gly Gln Glu Ser Gly Phe Thr Tyr Ser Arg Ser Gly
    50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Leu Ala Ala Thr Val Thr
                85                  90                  95

Ile Thr His Leu Leu Lys Ala Gly Asp Gln Ile Ile Cys Met Asp Asp
            100                 105                 110

Val Tyr Gly Gly Thr Asn Arg Tyr Phe Arg Gln Val Ala Ser Glu Phe
        115                 120                 125

Gly Leu Lys Ile Ser Phe Val Asp Cys Ser Lys Ile Lys Leu Leu Glu
    130                 135                 140

Ala Ala Ile Thr Pro Glu Thr Lys Leu Val Trp Ile Glu Thr Pro Thr
145                 150                 155                 160

Asn Pro Thr Gln Lys Val Ile Asp Ile Glu Ala Cys Ala His Ile Val
                165                 170                 175

His Lys His Gly Asp Ile Ile Leu Val Val Asp Asn Thr Phe Met Ser
            180                 185                 190

Pro Tyr Phe Gln Arg Pro Leu Ala Leu Gly Ala Asp Ile Cys Met Tyr
        195                 200                 205

Ser Ala Thr Lys Tyr Met Asn Gly His Ser Asp Val Val Ile Gly Leu
    210                 215                 220

Val Ser Val Asn Cys Glu Ser Leu His Asn Arg Leu Arg Phe Leu Gln
225                 230                 235                 240

Asn Ser Leu Gly Ala Val Pro Ser Pro Ile Asp Cys Tyr Leu Cys Asn
                245                 250                 255

Arg Gly Leu Lys Thr Leu His Val Arg Met Glu Lys His Phe Lys Asn
            260                 265                 270

Gly Met Ala Val Ala Gln Phe Leu Glu Ser Asn Pro Trp Val Glu Lys
        275                 280                 285

Val Ile Tyr Pro Gly Leu Pro Ser His Pro Gln His Glu Leu Val Lys
    290                 295                 300

Arg Gln Cys Thr Gly Cys Thr Gly Met Val Thr Phe Tyr Ile Lys Gly
305                 310                 315                 320

Thr Leu Gln His Ala Glu Ile Phe Leu Lys Asn Leu Lys Leu Phe Thr
                325                 330                 335

Leu Ala Val Ser Leu Gly Gly Phe Glu Ser Leu Ala Glu Leu Pro Ala
            340                 345                 350

Ile Met Thr His Ala Ser Val Leu Lys Asn Asp Arg Asp Val Leu Gly
        355                 360                 365
```

```
Ile Ser Asp Thr Leu Ile Arg Leu Ser Val Gly Leu Glu Asp Glu Glu
370                 375                 380

Asp Leu Leu Glu Asp Leu Asp Gln Ala Leu Lys Ala Ala His Pro Pro
385                 390                 395                 400

Ser Gly Ser His Ser
                405

<210> SEQ ID NO 7
<211> LENGTH: 405
<212> TYPE: PRT
<213> ORGANISM: Pongo abelii

<400> SEQUENCE: 7

Met Gln Glu Lys Glu Ala Ser Ser Gln Gly Phe Leu Pro His Phe Gln
1               5                   10                  15

His Phe Ala Thr Gln Ala Ile His Val Gly Gln Glu Pro Glu Gln Trp
                20                  25                  30

Thr Ser Arg Ala Val Val Pro Ile Ser Pro Ser Val Thr Phe Lys
            35                  40                  45

Gln Gly Ala Pro Gly Gln His Ser Gly Phe Val Tyr Ser Arg Ser Gly
    50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Leu Ala Ala Thr Val Thr
                85                  90                  95

Ile Thr His Leu Leu Lys Ala Gly Asp Gln Ile Ile Cys Met Asp Asp
                100                 105                 110

Val Tyr Ala Gly Thr Asn Arg Tyr Phe Arg Gln Val Ala Ser Glu Phe
            115                 120                 125

Gly Leu Lys Ile Ser Phe Val Asp Cys Ser Lys Ile Lys Leu Leu Glu
    130                 135                 140

Ala Ala Ile Thr Pro Glu Thr Lys Leu Val Trp Ile Glu Thr Pro Thr
145                 150                 155                 160

Asn Pro Thr Gln Lys Met Thr Asp Ile Glu Ala Cys His Ile Val
                165                 170                 175

His Lys His Gly Asp Ile Ile Leu Val Val Asp Asn Thr Phe Met Ser
                180                 185                 190

Pro Tyr Phe Gln Arg Pro Leu Ala Leu Gly Ala Asp Ile Cys Met Cys
            195                 200                 205

Ser Ala Thr Lys Tyr Met Asn Gly His Ser Asp Val Val Met Gly Leu
    210                 215                 220

Val Ser Val Asn Cys Glu Ser Leu Tyr Asn Arg Leu Arg Phe Leu Gln
225                 230                 235                 240

Asn Ser Leu Gly Ala Val Pro Ser Pro Ile Asp Cys Tyr Leu Cys Asn
                245                 250                 255

Arg Gly Leu Lys Thr Leu Gln Val Arg Met Glu Lys His Phe Lys Asn
            260                 265                 270

Gly Met Ala Val Ala Gln Phe Leu Glu Ser Asn Pro Trp Val Glu Lys
    275                 280                 285

Val Ile Tyr Pro Gly Leu Pro Ser His Pro Gln His Glu Leu Val Lys
290                 295                 300

Arg Gln Cys Thr Gly Cys Thr Gly Met Val Thr Phe Tyr Ile Lys Gly
305                 310                 315                 320

Thr Leu Gln His Ala Glu Ile Phe Leu Lys Asn Leu Lys Leu Phe Thr
                325                 330                 335
```

```
Leu Ala Glu Ser Leu Gly Gly Phe Glu Ser Leu Val Glu Leu Pro Ala
            340                 345                 350

Val Met Thr His Ala Ser Val Leu Lys Lys Asp Arg Asp Val Leu Gly
            355                 360                 365

Ile Ser Asp Thr Leu Ile Arg Leu Ser Val Gly Leu Glu Asp Glu Glu
            370                 375                 380

Asp Leu Leu Glu Asp Leu Asp Gln Ala Leu Lys Ala Ala His Pro Pro
385                 390                 395                 400

Ser Gly Ser His Ser
            405

<210> SEQ ID NO 8
<211> LENGTH: 405
<212> TYPE: PRT
<213> ORGANISM: Macaca fascicularis

<400> SEQUENCE: 8

Met Gln Glu Lys Asp Ala Ser Ser Gln Gly Phe Leu Pro His Phe Gln
1               5                   10                  15

His Phe Ala Thr Gln Ala Ile His Val Gly Gln Glu Pro Glu Gln Trp
            20                  25                  30

Thr Ser Arg Ala Val Val Pro Leu Ile Ser Leu Ser Thr Thr Phe Lys
        35                  40                  45

Gln Ala Ala Pro Gly Gln His Ser Gly Phe Glu Tyr Ser Arg Ser Gly
    50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Leu Ala Ala Thr Val Thr
                85                  90                  95

Ile Thr His Leu Leu Lys Ala Gly Asp Gln Ile Ile Cys Met Asp Asp
            100                 105                 110

Val Tyr Gly Gly Thr Asn Arg Tyr Phe Arg Gln Val Ala Ser Glu Phe
        115                 120                 125

Gly Leu Lys Ile Ser Phe Val Asp Cys Ser Lys Ile Lys Leu Leu Glu
    130                 135                 140

Ala Ala Ile Thr Pro Glu Thr Lys Leu Val Trp Ile Glu Thr Pro Thr
145                 150                 155                 160

Asn Pro Val Leu Lys Met Ile Asp Ile Glu Ala Cys Ala His Ile Val
                165                 170                 175

His Lys Arg Gly Asp Ile Ile Leu Val Val Asp Asn Thr Phe Met Ser
            180                 185                 190

Pro Tyr Phe Gln Arg Pro Leu Ala Leu Gly Ala Asp Ile Cys Met Cys
        195                 200                 205

Ser Ala Thr Lys Tyr Met Asn Gly His Ser Asp Val Val Met Gly Leu
    210                 215                 220

Val Ser Val Asn Cys Glu Arg Leu His Asn Arg Leu Arg Phe Leu Gln
225                 230                 235                 240

Asn Ser Leu Gly Ala Val Pro Ser Pro Leu Asp Cys Tyr Leu Cys Asn
                245                 250                 255

Arg Gly Leu Lys Thr Leu His Val Arg Met Glu Lys His Phe Lys Asn
            260                 265                 270

Gly Met Ala Val Ala Gln Phe Leu Glu Ser Asn Pro Gly Val Glu Lys
        275                 280                 285

Val Ile Tyr Pro Gly Leu Pro Ser His Pro Gln His Glu Leu Ala Lys
```

```
                290                 295                 300
Arg Gln Cys Thr Gly Cys Thr Gly Met Ile Thr Phe Tyr Ile Lys Gly
305                 310                 315                 320

Thr Leu Gln His Ala Glu Ile Phe Leu Lys Asn Leu Lys Leu Phe Thr
                325                 330                 335

Leu Ala Glu Ser Leu Gly Gly Phe Glu Ser Leu Val Glu Leu Pro Ala
                340                 345                 350

Ile Met Thr His Ala Ser Val Pro Lys Asn Asp Arg Asp Val Leu Gly
                355                 360                 365

Ile Ser Asp Thr Leu Ile Arg Leu Ser Val Gly Leu Glu Asp Glu Lys
                370                 375                 380

Asp Leu Leu Glu Asp Leu Asp Gln Ala Leu Lys Ala Ala His Pro Pro
385                 390                 395                 400

Ser Gly Ser His Asn
                405

<210> SEQ ID NO 9
<211> LENGTH: 405
<212> TYPE: PRT
<213> ORGANISM: Pan troglodytes

<400> SEQUENCE: 9

Met Gln Glu Lys Asp Ala Ser Ser Gln Gly Phe Leu Pro His Phe Gln
1               5                   10                  15

His Phe Ala Thr Gln Ala Ile His Val Gly Gln Asp Pro Glu Gln Trp
                20                  25                  30

Thr Ser Arg Ala Leu Val Pro Pro Ile Ser Leu Ser Thr Thr Phe Lys
            35                  40                  45

Gln Gly Ala Pro Gly Gln His Ser Gly Phe Glu Tyr Ser Arg Ser Gly
        50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Leu Ala Ala Thr Val Thr
                85                  90                  95

Ile Thr His Leu Leu Lys Ala Gly Asp Gln Ile Ile Cys Met Asp Asp
                100                 105                 110

Val Tyr Gly Gly Thr Asn Arg Tyr Phe Arg Gln Val Ala Ser Glu Phe
            115                 120                 125

Gly Leu Lys Ile Ser Phe Val Asp Cys Ser Lys Ile Lys Leu Leu Glu
        130                 135                 140

Ala Ala Ile Thr Pro Glu Thr Lys Leu Val Trp Ile Glu Thr Pro Thr
145                 150                 155                 160

Asn Pro Thr Gln Lys Val Ile Asp Ile Glu Ala Cys Ala His Ile Val
                165                 170                 175

His Lys His Gly Asp Ile Ile Leu Val Val Asp Asn Thr Phe Met Ser
                180                 185                 190

Pro Tyr Phe Gln Arg Pro Leu Ala Leu Gly Ala Asp Ile Cys Met Tyr
            195                 200                 205

Ser Ala Thr Lys Tyr Met Asn Gly His Ser Asp Val Val Met Gly Leu
        210                 215                 220

Val Ser Val Asn Cys Glu Ser Leu His Asn Arg Leu Arg Phe Leu Gln
225                 230                 235                 240

Asn Ser Leu Gly Ala Val Pro Ser Pro Ile Asp Cys Tyr Leu Cys Asn
                245                 250                 255
```

-continued

```
Arg Gly Leu Lys Thr Leu His Val Arg Met Glu Lys His Phe Lys Asn
            260                 265                 270

Gly Met Ala Val Ala Gln Phe Leu Glu Ser Asn Pro Trp Val Glu Lys
        275                 280                 285

Val Ile Tyr Pro Gly Leu Pro Ser His Pro Gln His Glu Leu Val Lys
        290                 295                 300

Arg Gln Cys Thr Gly Cys Thr Gly Met Val Thr Phe Tyr Ile Lys Gly
305                 310                 315                 320

Thr Leu Gln His Ala Glu Ile Phe Leu Lys Asn Leu Lys Leu Phe Thr
                325                 330                 335

Leu Ala Glu Ser Leu Gly Gly Phe Glu Ser Leu Ala Glu Leu Pro Ala
            340                 345                 350

Ile Met Thr His Ala Ser Val Leu Lys Asn Asp Arg Asp Val Leu Gly
            355                 360                 365

Ile Ser Asp Thr Leu Ile Arg Leu Ser Val Gly Leu Glu Asp Glu Glu
        370                 375                 380

Asp Leu Leu Glu Asp Leu Asp Gln Ala Leu Lys Ala Ala His Pro Pro
385                 390                 395                 400

Ser Gly Ser His Ser
                405

<210> SEQ ID NO 10
<211> LENGTH: 405
<212> TYPE: PRT
<213> ORGANISM: Pan paniscus

<400> SEQUENCE: 10

Met Gln Glu Lys Asp Ala Ser Ser Gln Gly Phe Leu Pro His Phe Gln
1               5                   10                  15

His Phe Ala Thr Gln Ala Ile His Val Gly Gln Asp Pro Glu Gln Trp
            20                  25                  30

Thr Ser Lys Ala Leu Val Pro Pro Ile Ser Leu Ser Thr Thr Phe Lys
        35                  40                  45

Gln Gly Ala Pro Gly Gln His Ser Gly Phe Glu Tyr Ser Arg Ser Gly
    50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Leu Ala Ala Thr Val Thr
                85                  90                  95

Ile Thr His Leu Leu Lys Ala Gly Asp Gln Ile Ile Cys Met Asp Asp
            100                 105                 110

Val Tyr Gly Gly Thr Asn Arg Tyr Phe Arg Gln Val Ala Ser Glu Phe
        115                 120                 125

Gly Leu Lys Ile Ser Phe Val Asp Cys Ser Lys Ile Lys Leu Leu Glu
    130                 135                 140

Ala Ala Ile Thr Pro Glu Thr Lys Leu Val Trp Ile Glu Thr Pro Thr
145                 150                 155                 160

Asn Pro Thr Gln Lys Val Ile Asp Ile Glu Ala Cys Ala His Ile Val
                165                 170                 175

His Lys His Gly Asp Ile Ile Leu Val Val Asp Asn Thr Phe Met Ser
            180                 185                 190

Pro Tyr Phe Gln Arg Pro Leu Ala Leu Gly Ala Asp Ile Cys Met Tyr
        195                 200                 205

Ser Ala Thr Lys Tyr Met Asn Gly His Ser Asp Val Val Ile Gly Leu
    210                 215                 220
```

```
Val Ser Val Asn Cys Glu Ser Leu His Asn Arg Leu Arg Phe Leu Gln
225                 230                 235                 240

Asn Ser Leu Gly Ala Val Pro Ser Pro Ile Asp Cys Tyr Leu Cys Asn
            245                 250                 255

Arg Gly Leu Lys Thr Leu His Val Arg Met Glu Lys His Phe Lys Asn
        260                 265                 270

Gly Met Ala Val Ala Gln Phe Leu Glu Ser Asn Pro Trp Val Glu Lys
    275                 280                 285

Val Ile Tyr Pro Gly Leu Pro Ser His Pro Gln His Glu Leu Val Lys
290                 295                 300

Arg Gln Cys Thr Gly Cys Thr Gly Met Val Thr Phe Tyr Ile Lys Gly
305                 310                 315                 320

Thr Leu Gln His Ala Glu Ile Phe Leu Lys Asn Leu Lys Leu Phe Thr
                325                 330                 335

Leu Ala Glu Ser Leu Gly Gly Phe Glu Ser Leu Ala Glu Leu Pro Ala
            340                 345                 350

Ile Met Thr His Ala Ser Val Leu Lys Asn Asp Arg Asp Val Leu Gly
        355                 360                 365

Ile Ser Asp Thr Leu Ile Arg Leu Ser Val Gly Leu Glu Asp Glu Glu
370                 375                 380

Asp Leu Leu Glu Asp Leu Asp Gln Ala Leu Lys Ala Ala His Pro Pro
385                 390                 395                 400

Ser Gly Ser His Ser
            405

<210> SEQ ID NO 11
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 11

Met Gln Glu Lys Asp Ala Ser Ser Gln Gly Phe Leu Pro His Phe Gln
1               5                   10                  15

His Phe Ala Thr Gln Ala Ile His Val Gly Gln Asp Pro Glu Gln Trp
            20                  25                  30

Thr Ser Arg Ala Val Val Pro Pro Ile Ser Leu Ser Thr Thr Phe Lys
        35                  40                  45

Gln Gly Ala Pro Gly Gln Glu Ser Gly Phe Thr Tyr Ser Arg Ser Gly
    50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Leu Ala Ala Thr Val Thr
                85                  90                  95

Ile Thr His Leu Leu Lys Ala Gly Asp Gln Ile Ile Cys Met Asp Asp
            100                 105                 110

Val Tyr Gly Gly Thr Asn Arg Tyr Phe Arg Gln Val Ala Ser Glu Phe
        115                 120                 125

Gly Leu Lys Ile Ser Phe Val Asp Cys Ser Lys Ile Lys Leu Leu Glu
    130                 135                 140

Ala Ala Ile Thr Pro Glu Thr Lys Leu Val Trp Ile Glu Thr Pro Thr
145                 150                 155                 160

Asn Pro Thr Gln Lys Val Ile Asp Ile Glu Gly Cys Ala His Ile Val
                165                 170                 175
```

His Lys His Gly Asp Ile Ile Leu Val Val Asp Asn Thr Phe Met Ser
            180                 185                 190

Pro Tyr Phe Gln Arg Pro Leu Ala Leu Gly Ala Asp Ile Ser Met Tyr
            195                 200                 205

Ser Ala Thr Lys Tyr Met Asn Gly His Ser Asp Val Val Met Gly Leu
        210                 215                 220

Val Ser Val Asn Cys Glu Ser Leu His Asn Arg Leu Arg Phe Leu Gln
225                 230                 235                 240

Asn Ser Leu Gly Ala Val Pro Ser Pro Ile Asp Cys Tyr Leu Cys Asn
                245                 250                 255

Arg Gly Leu Lys Thr Leu His Val Arg Met Glu Lys His Phe Lys Asn
                260                 265                 270

Gly Met Ala Val Ala Gln Phe Leu Glu Ser Asn Pro Trp Val Glu Lys
            275                 280                 285

Val Ile Tyr Pro Gly Leu Pro Ser His Pro Gln His Glu Leu Val Lys
        290                 295                 300

Arg Gln Cys Thr Gly Cys Thr Gly Met Val Thr Phe Tyr Ile Lys Gly
305                 310                 315                 320

Thr Leu Gln His Ala Glu Ile Phe Leu Lys Asn Leu Lys Leu Phe Asp
                325                 330                 335

Leu Ala Val Ser Leu Gly Gly Phe Glu Ser Leu Ala Glu Leu Pro Ala
                340                 345                 350

Ile Met Thr His Ala Ser Val Leu Lys Asn Asp Arg Asp Val Leu Gly
            355                 360                 365

Ile Ser Asp Thr Leu Ile Arg Leu Ser Val Gly Leu Glu Asp Glu Glu
        370                 375                 380

Asp Leu Leu Glu Asp Leu Asp Gln Ala Leu Lys Ala Ala His Pro Pro
385                 390                 395                 400

Ser Gly Ser His Ser
                405

<210> SEQ ID NO 12
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 12

Met Gln Glu Lys Glu Ala Ser Ser Gln Gly Phe Leu Pro His Phe Gln
1               5                   10                  15

His Phe Ala Thr Gln Ala Ile His Val Gly Gln Glu Pro Glu Gln Trp
            20                  25                  30

Thr Ser Arg Ala Val Val Pro Pro Ile Ser Pro Ser Val Thr Phe Lys
        35                  40                  45

Gln Gly Ala Pro Gly Gln Glu Ser Gly Phe Thr Tyr Ser Arg Ser Gly
    50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Leu Ala Ala Thr Val Thr
                85                  90                  95

Ile Thr His Leu Leu Lys Ala Gly Asp Gln Ile Ile Cys Met Asp Asp
            100                 105                 110

Val Tyr Ala Gly Thr Asn Arg Tyr Phe Arg Gln Val Ala Ser Glu Phe
        115                 120                 125

```
Gly Leu Lys Ile Ser Phe Val Asp Cys Ser Lys Ile Lys Leu Leu Glu
            130                 135                 140

Ala Ala Ile Thr Pro Glu Thr Lys Leu Val Trp Ile Glu Thr Pro Thr
145                 150                 155                 160

Asn Pro Thr Gln Lys Met Thr Asp Ile Glu Ala Cys Ala His Ile Val
                165                 170                 175

His Lys His Gly Asp Ile Ile Leu Val Val Asp Asn Thr Phe Met Ser
            180                 185                 190

Pro Tyr Phe Gln Arg Pro Leu Ala Leu Gly Ala Asp Ile Cys Met Cys
        195                 200                 205

Ser Ala Thr Lys Tyr Met Asn Gly His Ser Asp Val Val Met Gly Leu
210                 215                 220

Val Ser Val Asn Cys Glu Ser Leu Tyr Asn Arg Leu Arg Phe Leu Gln
225                 230                 235                 240

Asn Ser Leu Gly Ala Val Pro Ser Pro Ile Asp Cys Tyr Leu Cys Asn
                245                 250                 255

Arg Gly Leu Lys Thr Leu Gln Val Arg Met Glu Lys His Phe Lys Asn
            260                 265                 270

Gly Met Ala Val Ala Gln Phe Leu Glu Ser Asn Pro Trp Val Glu Lys
        275                 280                 285

Val Ile Tyr Pro Gly Leu Pro Ser His Pro Gln His Glu Leu Val Lys
290                 295                 300

Arg Gln Cys Thr Gly Cys Thr Gly Met Val Thr Phe Tyr Ile Lys Gly
305                 310                 315                 320

Thr Leu Gln His Ala Glu Ile Phe Leu Lys Asn Leu Lys Leu Phe Asp
                325                 330                 335

Leu Ala Val Ser Leu Gly Gly Phe Glu Ser Leu Val Gly Leu Pro Ala
            340                 345                 350

Val Met Thr His Ala Ser Val Leu Lys Lys Asp Arg Asp Val Leu Gly
        355                 360                 365

Ile Ser Asp Thr Leu Ile Arg Leu Ser Val Gly Leu Glu Asp Glu Glu
370                 375                 380

Asp Leu Leu Glu Asp Leu Asp Gln Ala Leu Lys Ala Ala His Pro Pro
385                 390                 395                 400

Ser Gly Ser His Ser
                405

<210> SEQ ID NO 13
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 13

Met Gln Glu Lys Asp Ala Ser Ser Gln Gly Phe Leu Pro His Phe Gln
1               5                   10                  15

His Phe Ala Thr Gln Ala Ile His Val Gly Gln Glu Pro Glu Gln Trp
            20                  25                  30

Thr Ser Arg Ala Val Val Pro Leu Ile Ser Leu Ser Thr Thr Phe Lys
        35                  40                  45

Gln Ala Ala Pro Gly Gln Glu Ser Gly Phe Thr Tyr Ser Arg Ser Gly
    50                  55                  60

Asn Pro Thr Arg Asn Cys Leu Glu Lys Ala Val Ala Ala Leu Asp Gly
65                  70                  75                  80
```

Ala Lys Tyr Cys Leu Ala Phe Ala Ser Gly Leu Ala Ala Thr Val Thr
            85                  90                  95

Ile Thr His Leu Leu Lys Ala Gly Asp Gln Ile Ile Cys Met Asp Asp
            100                 105                 110

Val Tyr Gly Gly Thr Asn Arg Tyr Phe Arg Gln Val Ala Ser Glu Phe
            115                 120                 125

Gly Leu Lys Ile Ser Phe Val Asp Cys Ser Lys Ile Lys Leu Leu Glu
            130                 135                 140

Ala Ala Ile Thr Pro Glu Thr Lys Leu Val Trp Ile Glu Thr Pro Thr
145                 150                 155                 160

Asn Pro Val Leu Lys Met Ile Asp Ile Glu Ala Cys Ala His Ile Val
                165                 170                 175

His Lys Arg Gly Asp Ile Ile Leu Val Val Asp Asn Thr Phe Met Ser
            180                 185                 190

Pro Tyr Phe Gln Arg Pro Leu Ala Leu Gly Ala Asp Ile Cys Met Cys
            195                 200                 205

Ser Ala Thr Lys Tyr Met Asn Gly His Ser Asp Val Val Met Gly Leu
            210                 215                 220

Val Ser Val Asn Cys Glu Arg Leu His Asn Arg Leu Arg Phe Leu Gln
225                 230                 235                 240

Asn Ser Leu Gly Ala Val Pro Ser Pro Leu Asp Cys Tyr Leu Cys Asn
                245                 250                 255

Arg Gly Leu Lys Thr Leu His Val Arg Met Glu Lys His Phe Lys Asn
            260                 265                 270

Gly Met Ala Val Ala Gln Phe Leu Glu Ser Asn Pro Gly Val Glu Lys
            275                 280                 285

Val Ile Tyr Pro Gly Leu Pro Ser His Pro Gln His Glu Leu Ala Lys
            290                 295                 300

Arg Gln Cys Thr Gly Cys Thr Gly Met Ile Thr Phe Tyr Ile Lys Gly
305                 310                 315                 320

Thr Leu Gln His Ala Glu Ile Phe Leu Lys Asn Leu Lys Leu Phe Asp
            325                 330                 335

Leu Ala Val Ser Leu Gly Gly Phe Glu Ser Leu Val Glu Leu Pro Ala
            340                 345                 350

Ile Met Thr His Ala Ser Val Pro Lys Asn Asp Arg Asp Val Leu Gly
            355                 360                 365

Ile Ser Asp Thr Leu Ile Arg Leu Ser Val Gly Leu Glu Asp Glu Lys
            370                 375                 380

Asp Leu Leu Glu Asp Leu Asp Gln Ala Leu Lys Ala Ala His Pro Pro
385                 390                 395                 400

Ser Gly Ser His Asn
            405

<210> SEQ ID NO 14
<211> LENGTH: 405
<212> TYPE: PRT
<213> ORGANISM: Artificial Sequence
<220> FEATURE:
<223> OTHER INFORMATION: Synthetic polypeptide

<400> SEQUENCE: 14

Met Gln Glu Lys Asp Ala Ser Ser Gln Gly Phe Leu Pro His Phe Gln
1               5                   10                  15

His Phe Ala Thr Gln Ala Ile His Val Gly Gln Asp Pro Glu Gln Trp
            20                  25                  30

```
Thr Ser Arg Ala Leu Val Pro Pro Ile Ser Leu Ser Thr Thr Phe Lys
        35                  40                  45

Gln Gly Ala Pro Gly Gln Glu Ser Gly Phe Thr Tyr Ser Arg Ser Gly
    50                  55                  60

Asn Pro Thr Arg Asn Cys Leu Glu Lys Ala Val Ala Ala Leu Asp Gly
 65                  70                  75                  80

Ala Lys Tyr Cys Leu Ala Phe Ala Ser Gly Leu Ala Ala Thr Val Thr
                85                  90                  95

Ile Thr His Leu Leu Lys Ala Gly Asp Gln Ile Ile Cys Met Asp Asp
                100                 105                 110

Val Tyr Gly Gly Thr Asn Arg Tyr Phe Arg Gln Val Ala Ser Glu Phe
                115                 120                 125

Gly Leu Lys Ile Ser Phe Val Asp Cys Ser Lys Ile Lys Leu Leu Glu
        130                 135                 140

Ala Ala Ile Thr Pro Glu Thr Lys Leu Val Trp Ile Glu Thr Pro Thr
145                 150                 155                 160

Asn Pro Thr Gln Lys Val Ile Asp Ile Glu Ala Cys Ala His Ile Val
                165                 170                 175

His Lys His Gly Asp Ile Ile Leu Val Val Asp Asn Thr Phe Met Ser
                180                 185                 190

Pro Tyr Phe Gln Arg Pro Leu Ala Leu Gly Ala Asp Ile Cys Met Tyr
            195                 200                 205

Ser Ala Thr Lys Tyr Met Asn Gly His Ser Asp Val Val Met Gly Leu
        210                 215                 220

Val Ser Val Asn Cys Glu Ser Leu His Asn Arg Leu Arg Phe Leu Gln
225                 230                 235                 240

Asn Ser Leu Gly Ala Val Pro Ser Pro Ile Asp Cys Tyr Leu Cys Asn
                245                 250                 255

Arg Gly Leu Lys Thr Leu His Val Arg Met Glu Lys His Phe Lys Asn
                260                 265                 270

Gly Met Ala Val Ala Gln Phe Leu Glu Ser Asn Pro Trp Val Glu Lys
        275                 280                 285

Val Ile Tyr Pro Gly Leu Pro Ser His Pro Gln His Glu Leu Val Lys
        290                 295                 300

Arg Gln Cys Thr Gly Cys Thr Gly Met Val Thr Phe Tyr Ile Lys Gly
305                 310                 315                 320

Thr Leu Gln His Ala Glu Ile Phe Leu Lys Asn Leu Lys Leu Phe Asp
                325                 330                 335

Leu Ala Val Ser Leu Gly Gly Phe Glu Ser Leu Ala Glu Leu Pro Ala
                340                 345                 350

Ile Met Thr His Ala Ser Val Leu Lys Asn Asp Arg Asp Val Leu Gly
                355                 360                 365

Ile Ser Asp Thr Leu Ile Arg Leu Ser Val Gly Leu Glu Asp Glu Glu
                370                 375                 380

Asp Leu Leu Glu Asp Leu Asp Gln Ala Leu Lys Ala Ala His Pro Pro
385                 390                 395                 400

Ser Gly Ser His Ser
                405

<210> SEQ ID NO 15
<211> LENGTH: 405
<212> TYPE: PRT
<213> ORGANISM: Artificial Sequence
<220> FEATURE:
```

<223> OTHER INFORMATION: Synthetic polypeptide

<400> SEQUENCE: 15

```
Met Gln Glu Lys Asp Ala Ser Ser Gln Gly Phe Leu Pro His Phe Gln
1               5                   10                  15

His Phe Ala Thr Gln Ala Ile His Val Gly Gln Asp Pro Glu Gln Trp
            20                  25                  30

Thr Ser Lys Ala Leu Val Pro Pro Ile Ser Leu Ser Thr Thr Phe Lys
        35                  40                  45

Gln Gly Ala Pro Gly Gln Glu Ser Gly Phe Thr Tyr Ser Arg Ser Gly
    50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Leu Ala Ala Thr Val Thr
                85                  90                  95

Ile Thr His Leu Leu Lys Ala Gly Asp Gln Ile Ile Cys Met Asp Asp
            100                 105                 110

Val Tyr Gly Gly Thr Asn Arg Tyr Phe Arg Gln Val Ala Ser Glu Phe
        115                 120                 125

Gly Leu Lys Ile Ser Phe Val Asp Cys Ser Lys Ile Lys Leu Leu Glu
    130                 135                 140

Ala Ala Ile Thr Pro Glu Thr Lys Leu Val Trp Ile Glu Thr Pro Thr
145                 150                 155                 160

Asn Pro Thr Gln Lys Val Ile Asp Ile Glu Ala Cys Ala His Ile Val
                165                 170                 175

His Lys His Gly Asp Ile Ile Leu Val Val Asp Asn Thr Phe Met Ser
            180                 185                 190

Pro Tyr Phe Gln Arg Pro Leu Ala Leu Gly Ala Asp Ile Cys Met Tyr
        195                 200                 205

Ser Ala Thr Lys Tyr Met Asn Gly His Ser Asp Val Val Ile Gly Leu
    210                 215                 220

Val Ser Val Asn Cys Glu Ser Leu His Asn Arg Leu Arg Phe Leu Gln
225                 230                 235                 240

Asn Ser Leu Gly Ala Val Pro Ser Pro Ile Asp Cys Tyr Leu Cys Asn
                245                 250                 255

Arg Gly Leu Lys Thr Leu His Val Arg Met Glu Lys His Phe Lys Asn
            260                 265                 270

Gly Met Ala Val Ala Gln Phe Leu Glu Ser Asn Pro Trp Val Glu Lys
        275                 280                 285

Val Ile Tyr Pro Gly Leu Pro Ser His Pro Gln His Glu Leu Val Lys
    290                 295                 300

Arg Gln Cys Thr Gly Cys Thr Gly Met Val Thr Phe Tyr Ile Lys Gly
305                 310                 315                 320

Thr Leu Gln His Ala Glu Ile Phe Leu Lys Asn Leu Lys Leu Phe Asp
                325                 330                 335

Leu Ala Val Ser Leu Gly Gly Phe Glu Ser Leu Ala Glu Leu Pro Ala
            340                 345                 350

Ile Met Thr His Ala Ser Val Leu Lys Asn Asp Arg Asp Val Leu Gly
        355                 360                 365

Ile Ser Asp Thr Leu Ile Arg Leu Ser Val Gly Leu Glu Asp Glu Glu
    370                 375                 380

Asp Leu Leu Glu Asp Leu Asp Gln Ala Leu Lys Ala Ala His Pro Pro
385                 390                 395                 400
```

Ser Gly Ser His Ser
              405

<210> SEQ ID NO 16
<211> LENGTH: 1215
<212> TYPE: DNA
<213> ORGANISM: Artificial Sequence
<220> FEATURE:
<223> OTHER INFORMATION: Synthetic polynucleotide

<400> SEQUENCE: 16
atgcaggaaa aggatgcgag ctcccaagga tttcttccgc atttccagca ttttgcgacg      60
caggcgatac acgtgggcca agacccggaa cagtggacgt cgcgtgcggt tgtaccgccg     120
attagcctga gcacgacctt taaacaaggt gcgccgggcc agcatagcgg ttttacctat     180
agccgtagcg gcaatcccac acggaattgc tggagaagg cggtggcggc tctggacggc      240
gcgaagtatt gccttgcgtt tgcgagcgga ttggcggcca ccgtgaccat tacccacctg     300
cttaaggctg ggaccagat atttgcatg atgatgtgt atggtgggac caataggtat        360
ttccgtcagg tggcgagcga gttcggcctg aagatatcct tgtcgactg ctcgaagatc      420
aagctgttag aggcagcgat tacgccggaa acaaaacttg tgtggataga accccgacg      480
aacccgaccc agaaagtgat tgacattgaa ggctgcgccc acattgtgca taaacacggc     540
gatatcatcc tggtcgtgga taataccttc atgagcccgt acttccagcg tccgctggcg     600
cttggcgccg acattagcat gtattcggcg accaagtata tgaacggcca tagcgacgtt     660
gtcatgggcc tggtgagcgt gaattgcgag agcctgcata atcgtctgcg ttttctgcaa     720
aattcgcttg gagcggtgcc gagcccgatc gattgctatc tgtgcaatcg tgggctgaag     780
actctgcatg tgcggatgga gaaacatttt aagaatggca tggctgtggc gcagtttctg     840
gaaagcaatc cgtgggtgga aaaagttatc tacccgggac tgcccagcca cccgcagcat     900
gaactggtca acgtcagtg cacaggttgc accggcatgg tgaccttcta tatcaagggc     960
accctgcaac acgccgaaat ctttctgaaa aacctgaaac tgtttaccct ggcagtgagc    1020
ttgggcggct ttgaaaagcct tgctgaactg ccggccatta tgactcatgc ctccgtgttg    1080
aaaaatgatc gtgatgttct gggcataagc gataccctga ttcgcctgtc cgtaggactg    1140
gaagatgaag aagatctgct ggaggatctg gatcaggcgc tgaaagcggc ccatccccca    1200
tcgggaagcc acagt                                                    1215

<210> SEQ ID NO 17
<211> LENGTH: 1215
<212> TYPE: DNA
<213> ORGANISM: Artificial Sequence
<220> FEATURE:
<223> OTHER INFORMATION: Synthetic polynucleotide

<400> SEQUENCE: 17
atgcaggaaa aggatgcgag ctcccaagga tttcttccgc atttccagca ttttgcgacg      60
caggcgatac acgtgggcca agacccggaa cagtggacgt cgcgtgcggt tgtaccgccg     120
attagcctga gcacgacctt taaacaaggt gcgccgggcc aggagagcgg ttttacctat     180
agccgtagcg gcaatcccac acggaattgc tggagaagg cggtggcggc tctggacggc      240
gcgaagtatt gccttgcgtt tgcgagcgga ttggcggcca ccgtgaccat tacccacctg     300
cttaaggctg ggaccagat atttgcatg atgatgtgt atggtgggac caataggtat        360
ttccgtcagg tggcgagcga gttcggcctg aagatatcct tgtcgactg ctcgaagatc      420

```
aagctgttag aggcagcgat tacgccggaa acaaaacttg tgtggataga aaccccgacg    480
aacccgaccc agaaagtgat tgacattgaa ggctgcgccc acattgtgca taaacacggc    540
gatatcatcc tggtcgtgga taataccttc atgagcccgt acttccagcg tccgctggcg    600
cttggcgccg acattagcat gtattcggcg accaagtata tgaacggcca tagcgacgtt    660
gtcatgggcc tggtgagcgt gaattgcgag agcctgcata atcgtctgcg ttttctgcaa    720
aattcgcttg gagcggtgcc gagcccgatc gattgctatc tgtgcaatcg tgggctgaag    780
actctgcatg tgcggatgga gaaacatttt aagaatggca tggctgtggc gcagtttctg    840
gaaagcaatc cgtgggtgga aaaagttatc tacccgggac tgcccagcca cccgcagcat    900
gaactggtca aacgtcagtg cacaggttgc accggcatgg tgaccttcta tatcaagggc    960
accctgcaac acgccgaaat ctttctgaaa aacctgaaac tgtttgatct ggcagtgagc   1020
ttgggcggct ttgaaagcct tgctgaactg ccggccatta tgactcatgc ctccgtgttg   1080
aaaaatgatc gtgatgttct gggcataagc gataccctga ttcgcctgtc cgtaggactg   1140
gaagatgaag aagatctgct ggaggatctg gatcaggcgc tgaaagcggc ccatccccca   1200
tcgggaagcc acagt                                                    1215
```